United States Patent
Al-Murrani et al.

(10) Patent No.: US 11,767,561 B2
(45) Date of Patent: Sep. 26, 2023

(54) PATTERN RECOGNITION RECEPTOR EXPRESSION AS A MEASURE OF SYSTEMIC HEALTH

(71) Applicant: Hill's Pet Nutrition, Inc., Topeka, KS (US)

(72) Inventors: Samer Al-Murrani, Topeka, KS (US); Dale S. Scherl, Lawrence, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 377 days.

(21) Appl. No.: 16/949,914

(22) Filed: Nov. 20, 2020

(65) Prior Publication Data

US 2021/0071254 A1 Mar. 11, 2021

Related U.S. Application Data

(62) Division of application No. 14/654,272, filed as application No. PCT/US2012/070936 on Dec. 20, 2012, now Pat. No. 10,876,161.

(51) Int. Cl.
*C12Q 1/68* (2018.01)
*C12Q 1/6883* (2018.01)
*G16B 25/00* (2019.01)
*G16H 50/20* (2018.01)

(52) U.S. Cl.
CPC .......... *C12Q 1/6883* (2013.01); *G16B 25/00* (2019.02); *G16H 50/20* (2018.01); *C12Q 2600/106* (2013.01); *C12Q 2600/158* (2013.01); *C12Q 2600/166* (2013.01); *Y02A 90/10* (2018.01)

(58) Field of Classification Search
CPC ................................................. C12Q 1/6813
See application file for complete search history.

(56) References Cited

U.S. PATENT DOCUMENTS

| | | | |
|---|---|---|---|
| 6,596,492 B2 | 7/2003 | Avery et al. | |
| 7,026,151 B2 | 4/2006 | Yamashita et al. | |
| 7,598,031 B2 | 10/2009 | Liew | |
| 7,766,658 B2 | 8/2010 | Tricca et al. | |
| 7,846,482 B2 | 12/2010 | Cupp et al. | |
| 7,873,482 B2 | 1/2011 | Stefanon et al. | |
| 8,722,080 B2 | 5/2014 | Hack | |
| 8,815,152 B2 | 8/2014 | Burgess-Cassler et al. | |
| 2003/0206874 A1 | 11/2003 | Doyle et al. | |
| 2004/0022786 A1 | 2/2004 | Dedea | |
| 2004/0023870 A1 | 2/2004 | Dedera et al. | |
| 2004/0136924 A1 | 7/2004 | Boyd et al. | |
| 2005/0158252 A1 | 7/2005 | Romanowski et al. | |
| 2005/0163727 A1 | 7/2005 | Doyle et al. | |
| 2006/0024246 A1 | 2/2006 | Maitra et al. | |
| 2006/0127329 A1 | 6/2006 | Xu et al. | |
| 2008/0260836 A1 | 10/2008 | Boyd | |

FOREIGN PATENT DOCUMENTS

WO 2011/130646 10/2011

OTHER PUBLICATIONS

Beklen et al., 2008, "Immunohistochemical localization of Toll-like receptors 1-10 in periodontitis," Oral Microbiol. Immunol. 23:425-431.
Bell, K. P. et al., "Dental hygienists' knowledge and opinions of oral-systemic connections: implications for education", J. Dent. Educ., Jun. 2012, 76:682-694.
Buduneli et al., 2011, "Salivary and plasma levels of toll-like receptor 2 and toll-like receptor 4 in chronic periodontitis," J. Periodontol. 82(6):878-884.
Dave, N. J. et al., "Systemic effects of periodontal disease in cats", Vet Q., 2012, 32:131-144, Published online Nov. 29, 2012.
Correa et al., 2010, "Effect of periodontal treatment on metabolic control, systemic inflammation and cytokines in patients with type 2 diabetes," J. Clin. Periodontol 37:53-58.
Crasta et al., 2009, "Bacteraemia due to dental flossing," J. Clin. Periodontol. 36:323-332.
Cullinan et al., 2009, "Periodontal disease and systemic health: current status," Australian Dental J. 54(1 Supp):S62-S69.
D'Aiuto et al., 2007, "Acute effects of periodontal therapy on bio-markers of vascular health," J Clin Periodontol. 34(2):124-129.
Debowes et al., 1996, "Association of periodontal disease and histologic lesions in multiple organs from 45 dogs," J. Vet. Dent. 13(2):57-60.
Deshpande et al., 1998, "Invasion of Aortic and Heart Endothelial Cells by Porphyromonas gingivalis," Infection and Immunity 66(11):5337-5343.
Dolieslager, SMJ. et al. The influence of oral bacteria on tissue levels of Toll-like receptor and cytokine mRNAs in feline chronic gingivostomatitis and oral health. Veterinary Immunology and Immunopathology, vol. 151, p. 263-274, 2013. Epub Dec. 12, 2012.
Forner et al., 2006, "Incidence of bacteremia after chewing, tooth brushing and scaling in individuals with periodontal inflammation," J. Clin. Periodontol. 33(6):401-407.
Gelani et al., 2009, "The role of toll-like receptor 2 in the recognition of Aggregatibacter actinomycetemcomitans," J. Periodontol. 80(12):2010-2019.

(Continued)

*Primary Examiner* — Kenneth R Horlick

(57) ABSTRACT

The present invention encompasses methods and kits employing pattern recognition receptor expression as a measure of systemic health in a subject afflicted with an oral health condition. In particular, the present invention is directed to methods involving measurement of the expression levels of one or more Pattern Recognition Receptors including but not limited to Toll-Like Receptors, myeloid differentiation primary response gene 88 (MyD88), and Nucleotide Binding oligomerization domain containing protein 1 (NOD1), in a companion animal, e.g., a dog or a cat, afflicted with an oral health condition. The described methods enable evaluation of the systemic health of the animal afflicted with an oral health condition by measuring expression levels of the indicated genes as compared to suitable controls.

20 Claims, No Drawings

Specification includes a Sequence Listing.

(56) References Cited

OTHER PUBLICATIONS

Gibson III et al., 2007, "Porphyromonas gingivalis mediated periodontal disease and atherosclerosis: disparate diseases with commonalities in pathogenesis through TLRs," Current Pharmaceutical Design 13(36):3665-3675.
Glickman et al., 2009, "Evaluation of the risk of endocarditis and other cardiovascular events on the basis of the severity of periodontal disease in dogs," J. Am Vet Med Assoc. 234(4):486-494.
Glickman et al., 2011, "Association between chronic azotemic kidney disease and the severity of periodontal disease in dogs," Preventive Veterinary Medicine 99(2-4):193-200.
Herzberg et al., 1996, "Effects of oral flora on platelets: possible consequences in cardiovascular disease," J. Periodontol. 67(10 Suppl):1138-1142.
Hofmann-Lehmann et al. Feline immunodeficiency virus (FIV) infection leads to increased incidence of feline odontoclastic resorptive lesions (FORL). Veterinary Immunology and immunopathology, vol. 65, p. 299-308, 1998.
Ide et al., 2003, "Effect of treatment of chronic periodontitis on levels of serum markers of acute-phase inflammatory and vascular responses," J Clin Periodontol. 30(4)334-340.
Ignacio et al., 2005, "Toll-like receptor expression in feline lymphoid tissues," Vet. Immunol. Immunopathol. 106(3-4):229-237.
International Search Report and Written Opinion in International Application No. PCT/US2012/070936, dated Aug. 2, 2013.
Jagannathan et al., 2009, "TLR cross-talk specifically regulates cytokine production by B cells from chronic inflammatory disease patients," J. Immunol. 183(11):7461-7470.
Janket et al., 2005, "Does periodontal treatment improve glycemic control in diabetic patients? A meta-analysis of intervention studies," J. Dent. Res. 84(12):1154-1159.
Jones et al., 2007, "Does periodontal care improve glycemic control? The Department of Veterans Affairs Dental Diabetes Study," J. Clin. Periodontol. 34:46-52.
Kawai et al., 2009, "The Roles of TLRs, RLRs and NLRs in Pathogen Recognition" International immunology 21(4):317-337.
Kinane et al., 2008, "Group E of European Workshop on Periodontology. Periodontal diseases and health: Consensus Report of the Sixth European Workshop on Periodontology," J Clinical Periodontol. 35(8 Suppl):333-337.
Lima et al., 2010, "The essential role of toll like receptor-4 in the control of Aggregatibacter actinomycetemcomitans infection in mice," J. Clin. Periodontol. 37(3):248-254.
Lockhart et al., 2008, "Bacteremia associated with toothbrushing and dental extraction," Circulation 117(24):3118-3125.
Logan, 1994, "Oral health assessment in dogs: parameters and methods," J. Vet. Dent. 11(2):58-63.
Mahanonda et al., 2007, "Toll-like receptors and their role in periodontal health and disease," Periodontol 2000 43:41-55.
Papapanou et al., 2007, "Periodontal therapy alters gene expression of peripheral blood monocytes," J Clin Periodontol. 34:736-747.
Papapanou, PN. et al. Periodontal therapy alters gene expression of peripheral blood monocytes. J Clin. Periodontology, vol. 34, p. 736-747, 2007.
Perez-Chaparro et al., 2008, "Genotypic characterization of Porphyromonas gingivalis isolated from subgingival plaque and blood sample in positive bacteremia subjects with periodontitis," J. Clin. Peroidontal. 35:748-753.
Ramamoorthy, R. D. et al., "A review of C-reactive protein: A diagnostic indicator in periodontal medicine", J. Pharm. Bioallied. Sci., Aug. 2012, 4(2):S422-S426.
Rawlinson et al., 2011, "Association of periodontal disease with systemic health indices in dogs and the systemic response to treatement of periodontal disease," J. Am. Vet Med Assoc. 238(5):601-609.
Rojo-Botello et al., 2012, "Expression of toll-like receptors 2, 4 and 9 is increased in gingival tissue from patients with type 2 diabetes and chronic periodontitis," J. Periodontal Research 47(1):62-73.
Rojo-Botello, NR et al. Expression of toll-like receptors 2,4 and 9 is increased in gingival tissue from patients with type 2 diabetes amd chronic periodontitis. J. Periodont Res., vol. 47: p. 62-73, 2012, Epub Aug. 17, 2011.
Sarah et al., 2006, "Expression of Toll-like receptors 2 and 4 in gingivitis and chronic periodontitis," Indian J. Dent. Res. 17(3):114-116.
Scannapieco et al., 2003, "Associations between periodontal disease and risk for atherosclerosis, cardiovascular disease, and stroke. A systematic review," Ann Periodontol. 8(1):38-53 Review.
Scannapieco, 1998, "Position paper of the American Academy of Periodontology: periodontal disease as a potential risk factor for systemic diseases," J. Periodontol. 69(7):841-850 Review.
Scannapieco, 2004, "Periodontal inflammation: from gingivitis to systemic disease?" Compend Contin Educ Dent. 25(7 Suppl 1):16-25.
Scannapieco, 2005, "Systemic effects of periodontal diseases," Dent Clin North Am. 49(3):533-250, vi. Review.
Scheres, N. et al., "Periodontal ligament and gingival fibroblasts from periodontitis patients are more active in interaction with Porphyromonas gingivalis", J. Periodontal. Res., 2011, 46:407-416.
Silver et al., 1975, "Recovery and clearance rates of oral microorganisms following experimental bacteraemias in dogs," Arch. Oral Biol. 20(10):675-679.
Silver et al., 1977, "Experimental transient bacteraemias in human subjects with varying degrees of plaque accumulation and gingival inflammation," J. Clin. Periodontol. 4(2):92-99.
Sorensen et al., 2008, "Blood cell gene expression profiling in subjects with aggressive periodontitis and chronic arthritis," J. Periodontol. 79(3):477-485.
Stewart et al., 2001, "The effect of periodontal treatment on glycemic control in patients with type 2 diabetes mellitus," J. Clin. Periodontol. 28(4):306-310.
Takeuchi et al., 1999, "Differential roles of TLR2 and TLR4 in recognition of gram-negative and gram-positive bacterial cell wall components," Immunity 11(4):443-451.
Teng et al., 2002, "Periodontal health and systemic disorders," J. Canadian Dental Assoc. 68(3):188-192.
Tonetti, 2009, "Periodontitis and risk for atherosclerosis: an update on intervention trials," J. Clin. Periodontol 36 (Suppl. 10):15-19.
Written Opinion in International Application No. PCT/US2012/070936, dated Nov. 19, 2014.
Yamaguchi et al., 2009, "Ability of supragingival plaque to induce toll-like receptor 4-mediated stimulation is associated with cytokine production by peripheral blood mononuclear cells," J. Periodontol. 80(3):512-520.
Yoshioka et al., 2008, "Analysis of the Activity to Induce Toll-Like Receptor (TLR)2-TLR4-Mediated Stimulation of Supragingival Plaque," J. Periodontal. 79(5):920-928.

SEQUENCE LISTING

<160> NUMBER OF SEQ ID NOS: 31

<210> SEQ ID NO 1
<211> LENGTH: 18
<212> TYPE: DNA
<213> ORGANISM: Felis catus

<400> SEQUENCE: 1
ggccctggac ctcagcta                                          18

<210> SEQ ID NO 2
<211> LENGTH: 16
<212> TYPE: DNA
<213> ORGANISM: Felis catus

<400> SEQUENCE: 2
gacccacgcc ctgcat                                            16

<210> SEQ ID NO 3
<211> LENGTH: 30
<212> TYPE: DNA
<213> ORGANISM: Felis catus

<400> SEQUENCE: 3

```
gaaaacctga ctatatcaga tgcacaaatg                                     30

<210> SEQ ID NO 4
<211> LENGTH: 31
<212> TYPE: DNA
<213> ORGANISM: Felis catus

<400> SEQUENCE: 4
agcaaaattt aaatgtttga atcttgtggg a                                   31

<210> SEQ ID NO 5
<211> LENGTH: 20
<212> TYPE: DNA
<213> ORGANISM: Felis catus

<400> SEQUENCE: 5
cacagtgttg ccgacatctc                                                20

<210> SEQ ID NO 6
<211> LENGTH: 21
<212> TYPE: DNA
<213> ORGANISM: Felis catus

<400> SEQUENCE: 6
ctcggtgatc agcaggaaga c                                              21

<210> SEQ ID NO 7
<211> LENGTH: 14
<212> TYPE: DNA
<213> ORGANISM: Felis catus

<400> SEQUENCE: 7
acggcgctgg ctga                                                      14

<210> SEQ ID NO 8
<211> LENGTH: 19
<212> TYPE: DNA
<213> ORGANISM: Felis catus

<400> SEQUENCE: 8
gctgccggat ctccaagta                                                 19

<210> SEQ ID NO 9
<211> LENGTH: 20
<212> TYPE: DNA
<213> ORGANISM: Felis catus

<400> SEQUENCE: 9
gctctgctgc ttgtcaccat                                                20

<210> SEQ ID NO 10
<211> LENGTH: 23
<212> TYPE: DNA
<213> ORGANISM: Felis catus

<400> SEQUENCE: 10
ggcagtcaca gtaacagtca aca                                            23

<210> SEQ ID NO 11
<211> LENGTH: 21
<212> TYPE: DNA
<213> ORGANISM: Felis catus

<400> SEQUENCE: 11
```

```
actgactcct gggtcttttg c                                              21

<210> SEQ ID NO 12
<211> LENGTH: 18
<212> TYPE: DNA
<213> ORGANISM: Felis catus

<400> SEQUENCE: 12
ccactctgcg gagcatca                                                  18

<210> SEQ ID NO 13
<211> LENGTH: 23
<212> TYPE: DNA
<213> ORGANISM: Felis catus

<400> SEQUENCE: 13
tctctgattg tcagctggaa cag                                            23

<210> SEQ ID NO 14
<211> LENGTH: 26
<212> TYPE: DNA
<213> ORGANISM: Felis catus

<400> SEQUENCE: 14
aggtggttgt gactcatatt tagcaa                                         26

<210> SEQ ID NO 15
<211> LENGTH: 25
<212> TYPE: DNA
<213> ORGANISM: Felis catus

<400> SEQUENCE: 15
ctattcaaca gcgtttgagg agcta                                          25

<210> SEQ ID NO 16
<211> LENGTH: 28
<212> TYPE: DNA
<213> ORGANISM: Felis catus

<400> SEQUENCE: 16
tgccttctga ttgaaagtaa tggctatt                                       28

<210> SEQ ID NO 17
<211> LENGTH: 2958
<212> TYPE: DNA
<213> ORGANISM: Felis catus

<400> SEQUENCE: 17
tgcgactggc tgttcctcaa gtccgtgccc cacttctcgg cggcagcgcc ccgtggtaac    60
gtcaccagcc tttccctgta ctccaaccgc atccaccacc tccacgactc cgactttgtc   120
cacctgtcca gctgcggcg tctcaacctc aaatggaact gcccaccgc cagcctcagc    180 cccatgcact tcccctgtca catgaccatt gagccccaca ccttcctggc cgtgcccacc   240
ctggaggagc tgaacctgag ctacaacagc atcacgacag tacccgccct gcccagttcc   300
ctcgtgtccc tgtccttgag ccgtaccaac atcctggtgc tggaccctgc caacctcgca   360
gggctgcact ccctgcgctt tctgttcctg gatggcaact gctactacaa gaaccccctgc   420 ccgcaggccc tgcaggtggc cccggggcgcc tccttggcc tgggcaacct tacgcacctg   480
tcactcaagt acaacaacct cactgcggtg ccccgcggcc tgcccccag cctggagtac   540
```

```
ctgctattgt cctacaacca catcatcacc ctggcacctg aggacctggc caacctgacc      600
gccctgcgtg tgctcgatgt gggtggaaac tgccgtcgct gtgaccacgc ccgcaacccc      660
tgtatggagt gccccaaggg cttcccgcac ctgcaccctg acaccttcag ccacctgaac      720
cacctcgaag gcctggtgtt gaaggacagc tctctctaca acctgaaccc cagatggttc      780
catgccctgg gcaacctcat ggtgctggac ctgagtgaga acttcctata tgactgcatc      840
accaaaacca cagccttcca gggcctggcc cagctgcgca gactcaactt gtctttcaat      900
taccacaaga aggtgtcctt tgcccacctg catctggcgc cctccttcgg gagcctgctc      960
tccctgcagc agctggacat gcatggcatc ttcttccgct cgctcagcga gaccacgctc     1020
cggtcgctgg tccacctgcc catgctccag agtctgcacc tgcagatgaa cttcatcaat     1080
caggcccagc tcagcatctt cggggccttc cctggcctgc gatacgtgga cctgtcagac     1140
aaccgcataa gtggagccat ggagctggcg gctgccacgg ggaggtgga tggtggggag      1200
agagtccggc tgccatctgg ggacctagct ctgggcccac cgggcacccc tagctccgag     1260
ggcttcatgc caggctgcaa gaccctcaac ttcaccttgg acctgtcacg gaacaaccta     1320
gtgacaatcc agccagagat gtttgcccgg ctctcgcgcc tccagtgcct gctcctgagc     1380
cgcaacagca tctcgcaggc agtcaacggc tcacaattta tgccgctgac cagcctgcag     1440
gtgctggacc tgtcccataa caagctggac ctgtaccatg gcgctctttt cacggagctg     1500
ccgcggctgg aggccctgga cctcagctac aacagccagc ccttcagcat gcagggcgtg     1560
ggtcacaacc tcagctttgt ggcacagctg ccggccctgc gctatctcag cctggcgcac     1620
aacgacatcc acgccgtgt gtcccagcag ctctgcagcg cctcgctgcg ggccttggac     1680
ttcagcggca tgccttgag ccggatgtgg gccgagggag acctgtatct ccgcttcttc     1740
cgaggcctga ggagcctggt ccggttggat ctgtcccaga atcgcctgca taccctcttg     1800
ccacgcaccc tggacaacct ccccaagagc ctgcggctgc tgcgtctccg tgacaattat     1860
ctggcttttct tcaactggag cagcctggtc ctcctcccca ggctggaagc cctgaccctg     1920
gcgggaaacc agctgaaggc cctgagcaac ggcagcttgc ctaatggaac ccagctccag     1980
aggctggacc tcagcagcaa cagtatcagc ttcgtggcct ccagctttt tgctctggcc     2040
accaggctgc gagagctcaa cctcagtgcc aacgccctca gacggtgga gccctcctgg     2100
ttcggttctc tagcgggcac cctgaaagtc ctagatgtga ctggcaaccc cctgcactgc     2160
gcctgtgggg cggccttcgt ggacttcttg ctggaggtgc aggctgcagt gcccggcctg     2220
ccaggccacg tcaagtgtgg cagtccaggt cagctccagg gccgcagcat ctttgcgcag     2280
gatctgcgcc tctgcctgga tgaggccctc tcctgggact gttttggcct ctcgctgctg     2340
accgtggccc tgggcctggc cgtgcccatg ctgcaccacc tctgtggctg ggacctctgg     2400
tactgcttcc acctgtgcct ggcctggctg ccccggcggg ggcggcggcg gggcgcggat     2460
gccctgccct acgatgcctt tgtggtcttc gacaaggcac agagcgcggt ggccgactgg     2520
gtgtacaacg agctgcgggt acggctagag gagcgccgtg gacgccgagc gctccgcctg     2580
tgcctggagg aacgtgactg gctacccggt aaaacgctct tgagaaacct gtgggcctca     2640
gtttacagca gccgcaagat gctgtttgtg ctggcccaca cagacagggt cagcggcctc     2700
ttgcgcgcca gctttctgct ggcccagcag cgcctgctgg aggaccgcaa ggacgttgtg     2760
gtgctggtga tcctgcgccc cgacgcccac cgctcccgct atgtgcggct gcgcagcgc     2820
ctctgccgcc agagcgtcct cctctggccc caccagccca gtggccagcg cagcttctgg     2880
gcccagctgg gcacggccct gaccagggac aaccagcact tctataacca gaacttctgc     2940
```

```
cggggcccca cgacggca                                                 2958
```

<210> SEQ ID NO 18
<211> LENGTH: 1780
<212> TYPE: DNA
<213> ORGANISM: Felis catus

<400> SEQUENCE: 18

```
accaactgct ccaacatgtc ccttagaaag gttcatgcag acttgacccc aaccacaacc     60
acactggatt tatcctacaa cctccttct cagcttcaga gttcagattt tcgttctgtc    120
tctaaactga aagttttgat tctgtgccac aacagaatcc aagagctgga tatcaagacc    180
tttgaattca acagagagtt aagatattta gatttgtctt acaacagatt gaagattgta    240
acttggtatt cactggcagg tctcagacat ttagatcttt cttcaatga ctttgacagt    300
gtgcctatcc acgaggaggc tggcaacatg tcacatctgg aaatcctggg tttgagtggg    360
gcaaaaatac gaaaatcaga tttccagaaa attgctcatt tgcatctaaa tacagtcttc    420
ttaggattaa gaagtctttc ttattatgaa gaaggtaacc tgcccatctt aaacacaaca    480
aaacttcata ttgttttacc aatgaacaca aatttctggg ttcttttgcg tgatggaatc    540
aagacttcaa aaatactaga aatgacaaac atagatggca aaagccaatt ttcaagttat    600
gaaactcaac aaaatcttac tttagcgaat tccaagacat ctattctatt gcttaataaa    660
gttgatttac tctgggacta ccttctcctc atcttccagt ttgtttggca tacatcagta    720
gaatgcttcc aagtccaaca tgtgactttt ggaggcaagg tttatcttga ccataattca    780
tttgattact caaatactgc aatgagagct ataaaattgg agcacataca gttcagaatt    840
ttttatattc cacaggaaag ggtctacttg cttttaccaa aatggatat agaaaacctg    900
actatatcag atgcacaaat gccacacatg cggtttccta attatcccac aagattcaaa    960
catttaaatt ttgctgataa tatcttaaca gatgacctgt ttaagcaacc tatccaattg   1020
cctcatttga aaactttaat tttgaagggc aataaattgg agacactttc tttagtgagt   1080
ttctttgcca acaacacatc cttgaagcac ttagatctca gccagaatct gttacaatat   1140
gaaaatgatg aaaattgctt ttggccagaa accttgatca ctatgaacct gtcatccaac   1200
aaatttgctg attctgtttt caggtgcttg cccagaagta ttcaaatact tgacctgaat   1260
aataacaaga ttcaaactgt ccctaaagag attattcatc tgaagtcttt gcgagaacta   1320
aatatcgcat ttaactttct aactgatctt cctgggtgca gtcatttcag aaaactctca   1380
attctgaaca ttgaaatgaa cttaattctc agcccatctc tggattttt ccagagctgt   1440
caggaagtta agactctgaa tgcaggaaga aacccattcc ggtgtacctg tgaattaaga   1500
gattttattc agctggaaaa atattcacag ggcatgatga ttggatggtc agattcatat   1560
atctgtgaat accctttgaa tctaaagggg actcggttaa aggatgttca tcttcctgaa   1620
ttatcttgca acacagctct gttgattgtc accattgtgg ttatcatgct agttctgggg   1680
actgctatgg ccttctgctg cctctacttt gatctgccct ggtatctcag gatgctaggt   1740
cagtggacac agacattgca gaggattagg aagacaacccc                         1780
```

<210> SEQ ID NO 19
<211> LENGTH: 1825
<212> TYPE: DNA
<213> ORGANISM: Felis catus

<400> SEQUENCE: 19

```
tgagccggta cacccagaag ctgcgacagc aactgggcct cgactccaag ttcatcctgt        60
gctacgccca gaaggaggag ctgttgctgg aggagctgta cacggacacc atcgtggagc       120
tggtgggctt caggaacgag agcctgggcc tgctgggcag cctggcctgc ctgctggacc       180
actccaccgg cgtcctcagc gagcaggcg agaccatctt catcttcggg gacgccggcg        240
tgggcaagtc catgctgctt cagcggctgc agggcctgtg ggccgcgggg ctgctggagg       300
cggagttcaa gttcttcttc cacttccgct gccgcgtgtt cagctgcttc aaggaggacg       360
acgcgctgtg cctgcaggac ctgctctttta agcattactg ctacccggag caggacccgg      420
atgaggtgtt cgccttcctg ctgcgcttcc cccacacggc cctcttcacc ttcgacggcc       480
tggacgagct gcactcggac ttcgacctga gcagcgtgcc tgacacctcc tcccctggg        540
agcccgccca ccccctggcc ctgctggcca acctgctcag cgggaagctg ctcaagggcg       600
ccgccaagct gctcacggcc cgcacgggca tcgagatccc gcgccagctc ctccgcaaga       660
aggtgtttct gcggggcttc tcgcccagcc agctgcgggc ctacacccag agggtgttcc       720
ccgagcccac cgtgcgggac cgcgtgctgg cccacctgga ggccaacccc aacctctgca       780
gcctgtgcgc cgtgcccctc ttctgctgga tcgtcttccg ctgtttccag cacttccaca       840
gtgttgccga catctccacg cagctgcctg actgcacggt gaccctgacc gacgtcttcc       900
tgctgatcac cgaggtccac ctgaacagga cgcagcccac cagcctggtc cagcggaaca       960
cgcgcagcca gacggagacc ttccgcgccg cggcgcgcc cttgcgctcg ctggggcggg      1020
tggcccacca gggcatggag aagaacctct ttgtctttgg ccaggaggac gtgcgggccg      1080
ccgaggtgca ggacggagag ctgcagctgg gcttcctgcg ggccgtgcca gagcagggcc      1140
tcggggggtga ccagcaggcc tatgagtttt tccacgtcac cctccaggcc ttctttaccg      1200
ccttctttct cgcggcggac gacaaggtag gcacgcagca gctgctcggg ttcttccggg      1260
agtgtgggct tcctggcgag gcggctgccg agtcctgcta cccctccttt ctccctgtgc      1320
ggtgtctgag gggccccggc ctggccgggg aggacctctt caagaacaag atcacttcc      1380
agttcaccaa cctcttcctg tgcgggctgt tgtccaaggc caagcagaaa ctcctgcggc      1440
acctggtgcc cgccgcggtc ctgcggagaa agcgcaaggc cctgtgggcg cacctgtttg      1500
ccagcctgcg ggcccacctg aagagcctgc cccggctcca gtacgagggc tacaaccagg      1560
tgcaggccat gccaccttc atctggatgc tgcgctgcat ctacgagacg cagagcgaga      1620
aggtggggcg gctggcggcc aagggcatct gtgcgaacta cctcaagctg acctactgca      1680
acgcctgctc ggccgactgc agcgccctct cgttcgtcct gcaccacctc cgcaagcggc      1740
tcgccctgga cctggacaac aacaacctca acgactacgg cgtgcgggag ctgcagccct      1800
gcttcagccg cctcacggtc atcag                                          1825
```

<210> SEQ ID NO 20
<211> LENGTH: 334
<212> TYPE: DNA
<213> ORGANISM: Felis catus

<400> SEQUENCE: 20

```
cccgccatgg ccgccggagg ctcccgcgcg gggtccgcgt cccccatccc ctcggcgtcc        60
tccctgcctc tagctgccct caacgtgcga gtgcggcgcc gcctgtcgct gttcctgaac       120
gtgcggacgc aggtggcggc cgactggacg gcgctggctg aggagatggg cttcgagtac       180
ttggagatcc ggcagctgga ggcgcatgcc gaccccatgg gcaagctcct ggacgactgg       240
cagggacgcc cgggagcctc ggtgggccgt ctgctggagc tgctcaccaa gctgggccgc       300
```

```
gatgacgtgc tggtggaact ggggcccagc atcg                                   334
```

<210> SEQ ID NO 21
<211> LENGTH: 1023
<212> TYPE: DNA
<213> ORGANISM: Felis catus

<400> SEQUENCE: 21

```
gaaggagatt gctcttggac tacaagttta ttaagtttaa atatgtcttc aaatatactt        60
acggactctg ttttcagatg tttacctcct aaggtcaagg tacttgatct tcacaataac       120
caaataagaa gcattcctaa accaatcatg aaactagaag ctttgcaaga actcaatgtt       180
gcctccaatt ccttagccca ccttcctgac tgtggagctt ttagcagcct ttctgtactg       240
atcattgacc ataattcaat ttccaaccca tcagctgatt tcttccacag ctgccagaag       300
attaggtcca taagagcagg aaacaatcca ttccaatgca cctgtgagct aagagaattt       360
atccagaata taggccaagc atcaagtgaa gtggtagagg gttggcctga ttcttataag       420
tgtgactatc agaaagtta aagggaacc ccactaaagg actttcatgt gtctcagtta        480
tcctgcaaca cagctctgct gcttgtcacc attggggtca ctgtgctggt gttgactgtt       540
actgtgactg ccctctgtat gtactttgat ctgccctggt atctcaggat ggtgtgtcag       600
tggacccaga cccggcacag ggcaaggaaa ctacccttag aagaactcca agaacccttt       660
cagttccacg cttttatttc atatagtggg catgattctg tgtgggtgaa gagtgaatta       720
ttaccaaacc tagaaaaaga agacctaagg atttgtctcc atgagagaaa ctttgttcct       780
ggcaagagca ttgtggagaa tatcatcaac tgcattgaaa aaagttacaa gtccatcttt       840
gttttgtctc ccaactttgt tcagagtgag tggtgtcatt atgaactcta ctttgcccac       900
cacaatctat ttcatgaagg ttttgataac ttaatttaa tcttgctgga gcctattcca        960
cagtattcca ttcctagcag ctatcacaag ctcaaaaatc tcatggcacg aaggacttat      1020
ttg                                                                   1023
```

<210> SEQ ID NO 22
<211> LENGTH: 2890
<212> TYPE: DNA
<213> ORGANISM: Felis catus

<400> SEQUENCE: 22

```
ggaatcatga gccagagttc gccttatatc tattccttt tggggctgtt gccctttgg         60
atactgtgta catcctccac caacaaatgt gttgttaggc atgaagcagc tgactgcagt       120
catctgaagt tgacacaagt gcccgatgac ctcccagcaa acataacggt gttgaatctc       180
acccataacc agctcagaag attaccgcct gacaacttta caagatatag ccaacttact       240
accttggatg gaggatttaa ctccatctca aaactggagc cagaattgtg ccaaaaactc       300
cccttgttgg aaattttgaa cctcgaacac aatgaactct ctcacctttc agagcgaact       360
tttatcttct gcgtgaattt gatggaactc catctaaggt ccaattcaat ccagaaaatt       420
gaaaacgatc ccttccaaaa cctgaagaat ttaatcaaat tagatctatc tcataatggt       480
ttgtcatcta ccaaattagg aagtcagctc caactggaaa atctccaaga gctcctgtta       540
tcaaataata aaattaacag cctgagacgt gaagaactgg atttccttgg caattcttct       600
ttgaagaaat tagaattgtc atcaaatcca attaaagagt tctctccagg tgtttttcat       660
gcaattggaa aactatttgg cctctctctg aacaatgctc aactgaaccc caacctcaca       720
```

```
gagcagcttt gtttagaact gtcgaacacg agcattcaga atctatcgct gagcaacacc    780
cagctgtaca gaacgagcaa tatgactttc gttgggctca agcacacaaa tctcaccgtg    840
ctcgatcttt cccacaacaa cttaaatgtg attgataatg gttccttcgt ttggcttcca    900
cgtctagaat atttcttcct ggggtataat aatatagaac acttatttc tcactccttg     960
tatgggcttc tcagtgtgag atacttggat ttgagacgat ctttcaccaa acaaagcact   1020
gctcttactt cgcgtcccaa gatcgatgat ttttcctttc agtggctaaa atgtttggag   1080
tatcttaaca tgggagacaa caacttccca ggcataagaa gcaatatgtt cacggggctg   1140
ataaagctga aacacttgag tctatccgac tccttcacaa gcttgcgaac tttaacaaat   1200
gaaacatttt tgtcacttgc tcagtctcct ttggtcacgc tcaacctaac caaaaacaaa   1260
atctcaaaaa tagagagtgg cgcttttttct tgtctgggcc accttcaggt actcgacctt   1320
ggccttaatg aaattgggca agagctcaca ggccaagaat ggagaggtct aggaaatatc   1380
attgaaatct acctttccta caacaaatac ctacaactga ctcctgggtc ttttgccctg   1440
gttccaagcc tccaacgcct gatgctccgc agagtggccc tgagaaatgt ggacagttct   1500
ccttcacctt ttcattctct tgcaacttg gtcattctgg atctaagcaa caacaatata    1560
gccaacataa atgataaact gttggagggt cttgagaaac tagaaattct ggaattgcag   1620
cacaacaact tagcacggct atggaaacgt gcaaacccta gtggtcctgt ttatttccta   1680
aagggtcttt ctccacctcca cattcttaac ttagagtcta atggctttga tgagatccca   1740
gcagaggtat tcaagggctt atctgaatta aagagcattg atttaggatt gaataattta   1800
aacatatttc cgctatctgt ctttgatgat caggcatctc taaagtcact gaaccttcag   1860
aagaatctca taacgtcagt tgagaaggat gttttttgggc cagccttcag gaacctgagt   1920
aatttagata tgagctttaa cccatttgat tgtacctgtg aaagtattgc ctggtttgtt   1980
aattggatta atagtaccca taccaacatc tctgacctgt caagccatta cctctgtaat   2040
actccacctc aatatcatgg tttcccggtg atgctttttg atatatcagc ctgcaaagac   2100
agtgccccct ttgaactctt tttcataata aataccagta tccttttgat tttcatcttt   2160
accgtattgc tcatccattt cgaaggctgg aggatatctt tttattggaa tgtttcagtg   2220
catcgagttc ttggtttcaa agaaatagac agacagccag agcagtttga atatgcagca   2280
tatataattc atgcctataa agatagagat tgggtctggg agaacttctc tccgatggaa   2340
gaaaaagatc aaactctcag attttgtctc gaagaaaggg actttgaggc aggtgtcctt   2400
gaacttgaat caattgttaa tagcatcaaa aggagcagaa aaactatttt cgttataacg   2460
cagcatctat taaagatcc attgtgtaaa agattcaagg tgcaccaggc agttcagcaa    2520
gctgtggaac aaaatctgga ttccattata ttgatctttc ttgaggatat tccagattat   2580
aaactgaacc atgcactctg tttgcgacga gggatgttta atctcactg catcttgaac    2640
tggccagttc agaagaacg ggtaaatgcc tttcatcata aattgcaagt agcgcttgga    2700
tccagaaatt caatacatta aatttattta aagactaagt taacaaaggc gtaactttcc   2760
cccacttaaa gagtttcata gtaaatttag gttttatttg aaaataatat acatctgttt   2820
attcagactt agagaggttt ctgataatta tatttggagt tttttttggga tgcactcata   2880
ggaaaataag                                                          2890

<210> SEQ ID NO 23
<211> LENGTH: 3113
<212> TYPE: DNA
<213> ORGANISM: Felis catus
```

<400> SEQUENCE: 23

```
agaatgatgc ctcctacccg cctggctggg actctgatcc cagccatggc cttcctctcc      60
tgcctgagac ctgagagctg ggacccttgt gtggaggtgg ttcctaacat tacttaccaa     120
tgcatggacc tgaatcttca caaaatcccc gacaacatcc cctcatcaac caaggacctg     180
gacatgagct ttaacccccct gagaaattta ggcagccata gtttctccaa cttcccagaa    240
ctgcaggtgc tggatttatc caggtgtgaa attcaaataa ttgaagatga tgcatatcag     300
ggcctaaacc acctctccat cttgatattg acaggaaatc ctatccagag gttattccca     360
ggagcttttt ctggactatc aagtttacag acgctggtgg ctgtgagac aaacatagca      420
tctctagagg acttcccat ggacatctc aaaacgttga aggagcttaa tgtggctcac       480
aatcttatcc attccttcaa attacctgaa tattttttcta acatgtccaa ccttgagtat    540
ttggatcttt ccaataacaa gattcaaaat atttatcata aagacttaca ggttctacat     600
caaaagcctc tactcaacct ttctttagac ttgtccctca acccttttaga ctttatccaa    660
ccaggtgcct ttaaagaagt taagctccgt gaactgactt tgagaagtaa ttttaatagt     720
acagatgtaa tgaaagcttc tattcaaggt ctggcaggtt tacagatcca tcagttggtt    780
ctgggagaat ttaaaaatga aggaacttg gaagatttg acaaatctat cctggaggga      840
ctgtgcaatt tgatcataga aaaattccgg atagcatact ttgacaagtt ctcagaggat    900
gctattgact catttaattg tttggcaaac gtttctacca tttctctggt gcatctgtat    960
ttcaagggc taaacagct ccctaaaaat ctcggatggc aacggttaga attggttaac     1020
tgtgaatttg aacaattcc cacatggaag ctggaccctc tcaaggagct tgttttctcc    1080
gccaacgaag ttaggaacgc ttttactcag gttaagttgg aaagccttga gtttctagac    1140
ctcagtagaa atgactttag tttgaagagt tgctgttctg agagagattt ggggacaacc   1200
agactgaagc atttagatct aagcttcaac aatattatta ccataagttc aaacttcttg   1260
ggcttagaac agttagaata tctagacttc cagcattcca gtttgaaaca ggtcagtgat   1320
ttttcagtat tcctacccct caaaaacctc cgttaccttg atatttctta cactcatacc   1380
caagttgcct tccatggcat cttcaatggc ttgatcagcc tccaaatctt aaaaatggct   1440
ggcaattctt tccaggacaa cttccttcca aatattttca tggagctgac taacttgacc   1500
attctagacc tctctgattg tcagctggaa caggtgtccc aagtggcatt taactcactc   1560
cctaaacttc agttgctaaa tatgagtcac aaccacctct tatcattgga tacacttcct   1620
tatgaaccte ttcactccct ccagactctg gactgcagtt ttaatcgtat agtggcctct   1680
aaggagcaag aactacggca ttttccaagt aatctatctt ccttaaatct tactcggaat   1740
gattttgctt gtgtttgtga acaccagagt ttcctgcagt gggtcaagga ccagaggcag   1800
ctcttggtgg aagttgaaca gatggtgtgt gcaaaacctt ggacatgca gggcatgccc    1860
atgctgaatt taggaatgc tacctgtcag gtgagaaaga ccatcattac tgggtcggtt    1920
ttcactgtac tcttggtttt tctggtggtg gttctggtgt ataagttcta tttccacctg   1980
atgcttcttg ctggctgtaa aaagtatagc agaggtgaaa gcacctatga tgccttcgtt   2040
atctactcaa gccaggatga agattgggtg aggaatgaat tggtaaagaa cttggaggag   2100
ggggtgcccc cttttcagct ctgccttcac tacagagact ttattcctgg tgtggccatc   2160
gccgccaaca tcatccagga aggtttccat aaaagccgga agttatcgt cgtggtgtcc   2220
cagcacttta tccagagtcg atggtgcatc tttgagtatg ggattgccca gacttggcag   2280
```

```
tttctcagca gccgtgccgg catcatcttc atcgtcctgc agaagttgga gaagtccctg    2340
ctgcggcagc aggtggagct gtatcgcctt ctcaacagga acacctacct ggagtgggag    2400
gacagtgtcc tggggaggca catcttctgg agacgactca gaaaagcctt gctggacggt    2460
aaaccacgct gtccagaagg aatggcagat gcagaaggca gctagcgtgg aagagtaacc    2520
tctgcctgag gaggaaacac tcctgcagtg cttcttgccc agctggaccc agtaccttcg    2580
ttcactaaat gagaattgaa tgctgtgaca tacctggcgc tgtgccaagg gcagatgatt    2640
cagtggtgcc cgaggaaccc aggactgctg acctcatggg gtttacagtg caggggagt    2700 aagtactgtg ctaaattaca gaatctccag gtggatgttt caaccaaatc agctaaggag    2760
tccatggcaa ggaaagtcaa ctcaacactt accccatcaa actgaattag acctaagacc    2820
ctgggcccta gtgaaatcag gagaaggtat agttcttcac ctgagtcttc tgaatggaaa    2880
ctacctcatg ttttacattt tagccagctt aaatttaact gaatgaggtc tttactcact    2940 tttcccttt ctattgaatg caatttaaat tccacttgat aactcagaag gctcctgatt    3000
gagaccacct cctctccaat ttcaacctgt ttccttacat aggctaaagt ctgtaactaa    3060
ttccgaagga atctgagta atacatatcc acaaacaaaa aaaaaaaaaa aaa           3113
```

<210> SEQ ID NO 24
<211> LENGTH: 3706
<212> TYPE: DNA
<213> ORGANISM: Felis catus

<400> SEQUENCE: 24

```
atttcatcgt ggaggaagac tgaacatggt gtttccaatg tgggcattga agagacagtc      60
ccttatcctt tttaacataa tcctaatttc caaactcctt ggagctagat ggtttcccaa     120
aactctgccc tgtgatgtca ctctggatgc tccaaaggcc catgtgattg tggactgcac     180
agacaagcat ttgacagaaa ttcctgaagg tattcctacc aatgccacca acctcaccct     240
caccatcaac cacataccctg gtatctctcc agcttccttc caccagctgg actacctggt     300
agagatcgat ttcagatgca actgtatacc tattcgactt gggccaaaag acaatatgtg     360
tcccaggagg ctgcagatta aacccagaag ctttagtaga ctcacttact taaaatccct     420
ttatctggat ggaaaccagc ttctagaaat acctgagggt cttccccca acttgcagct     480 gctgagcctt gaggccaaca gtatcttttg tatcatgaaa aataacctaa cagaactgac     540
caacatagaa aaactctact gggccaaaaa ctgttatttt cgcaatcctt gcaacgtttc     600 attttttcata gaaaagatg ctttcctgag tctgaaaaat ctaaaattgc tctccctaaa     660
agataacaat atcacatatg tccccactac attgccatcc actttaacag aactccatct     720
ttataacaac gccattgcaa aaatccaaga agatgatttt cataacctca atcaactgca     780
aattcttgac ctaggtggaa actgccctcg ttgttacaat gtcccatttc cttgtacacc     840
ctgtgagaac aattctcccc tacagatcca catgaaggcc tttgatgcat gacagaatt     900 acaagtttta cgtctataca gtaactctct tcagcatgtg ccccaaagat ggtttaaaaa     960
cattaaaaaa cttaaggagc tagatctttc acaaaacttc ttggccaaag aaattgggga    1020
tgccaaattt ttgcttcttc ttcacaacct tgtccaattg atctgtcttc aattatga       1080 acttcaggtc tatcgtgcaa ctctgaatct atcggatgca ttttcttcac tgaaaaacct    1140
gaaagtttta cggatcaaag gatacgtctt taaggagctg agcagccata acctctcccc    1200
gttacgtagt ctctccaatc ttgaagttct tgatcttggc actaacttca taaaaatcgc    1260
tgacctcagc atattcgaac aatttaaaac attgaaagtc atagatcttt caatgaataa    1320
```

```
aatatcacct tcaggagatt caagtgaagt tggcttctgc tctaacacca gaacttctgt    1380
agatggtaat gcacctcagg tccttgaaac attacattat ttcagatatg atgagtatgc    1440
aaggagttgc aggttcaaaa acaaagagac tccctctttc ttgcctttta ataaagattg    1500
ttatgtgtat gggcaggcac tggacctaag tagaaataat atattttttg tcaagtcctc    1560
tgattttcag catctgtctt tcctcaaatg cctaaacttg tcaggaaata ccattggcca    1620
aactctcaat ggcagtgaat ttcagccttt agtggagttg aagtatttgg acttctttaa    1680
caaccggctt gatttactct attcaacagc gtttgaggag ctacgcaacc tggaaattct    1740
agatataagt agtaatagcc attactttca atcagaaggc attactcaca tgctaaactt    1800
caccaagaac ctaaaagttc tgaagaaact catgatgaac aacaatgaca tctctatgtc    1860
caccagcagg accatggaga gtgagtctct tagaattctg gaattcagag gaaatcatttt   1920 ggatgtttta tggagagatg gtgataacag gtacttaaaa ttcttcaaga atctgctaaa    1980
cttagaggag ttagacatct ctgaaaattc cctgagtttc ttgccttctg gcgttttga    2040 tggcatgcct ccaaaactaa agactctctc cttggtcaaa aatgggctca gtccttcaa    2100 ctggggaaga ctccagtatc tgaagaatct agaaactttg gacctcagct acaatgagct    2160
gaagagtgtc cctgagagat tatacaactg ttccagaagt ctcaagaaac tgattctcaa    2220
gtacaatcaa atcaggcatc tgacaaagca ttttctacaa gatgctttcc agttgcgata    2280
cctggaccct agctcaaata aaatccagat tatccagaag actagctttc agaaaatgt    2340 cctcaataat ctgagagtgt tactttttgca tcataatcgg tttctgtgca cctgtgatgc    2400
tgtgtggttt gtctggtggg ttaaccatac agaggtgact attccttact tggccacaga    2460
tgtgacttgt gtggggccag gagcacacag gggccagagt gtggtctctc tggatctgta    2520
tacctgtgag gtagatctga ctaacctgat cctgttttca ctttccgtat cggtggctct    2580
ttctctgatg gtgattacaa cagcaaacca cctctatttc tgggatgtgt ggtatagtta    2640
ccatttctgt aaggccaaaa taaggggta tcagcgtctg acatcactgg attcttgcta   2700
cgatgccttt gttgtgtatg acactaaaga cccagcagtg acagagtggg ttttggatga    2760
gctggtggcc aagttggaag acccaagaga gaaacatttt aatctgtgtc ttgaggaaag    2820
ggattggcta ccagggcagc cagttctgga aaacctttcc cagagcatcc agcttagcaa    2880
aaagacggtg tttgtgatga caaacaagta tgcaaagacc gagaacttta agatcgcatt    2940
ttacttatcc catcagaggc tcatggatga aaaagtagac gtaattatct tgatattcct    3000
tgagaagccc cttcagaaat ccaagttcct ccagctccgg aagaggctgt gtaagagttc    3060
tgtccttgag tggccgacaa acccacaggc ccacccgtac ttctggcagt gtctgaaaaa    3120
tgccctggcc acagacaatc acgtgaccta tagtcaggtg ttcaaagaga cggtctagcc    3180
cttctttgcc cagcgtgact gcctgaccta ccaaggaaaa gcttggctgt ctagattgtc    3240
ccatgaatgc ctcactaaaa gggtgttgtt aaagtctcca agacctggga ttgtccacat    3300
cagagaggcg agtcacagtg tatgacaaag gaattggaaa aatggaattt ctataatgca    3360
tcacatcatc tttccgatct ctctgtgact ccattggcac ttgagtctcc cctttctgtt    3420
tctgtataag acacgactgg gagaagggcg gcaaggagag gacataaggc tctgattctc    3480
ctgtaattct cttgtgatta ttaaatacac acgcaatcac gaaattcaga ggaatcgtgc    3540
ttctactcct aagaagtacc gctctgtatg gaaatagggt aaaagatgct cagggcctac    3600
gtgtatgaca tcacaatgta ccagagttag tgaaatgaaa acacagggaa cgcaactgat    3660
```

<210> SEQ ID NO 25
<211> LENGTH: 1253
<212> TYPE: DNA
<213> ORGANISM: Canis familiaris
<220> FEATURE:
<221> NAME/KEY: misc_feature
<222> LOCATION: (721)..(721)
<223> OTHER INFORMATION: n is a, c, g, or t

<400> SEQUENCE: 25

```
ccttcagcat gcggggcgtg ggccacaatc tcagctttgt ggcacagctg ccggccctgc    60
gctacctcag cctggcgcac aatggcatcc acagccgcgt gtcccagcag ctccgcagcg   120
cctcgctccg ggccctggac ttcagtggca atacccctgag ccagatgtgg gccgagggag   180
acctctatct ccgcttcttc caaggcctga gaagcctggt tcagctggac ctgtcccaga   240
atcgcctgca tacctcctg ccacgcaacc tggacaacct ccccaagagc ctgcggctcc   300
tgcggctccg tgacaattac ctggcttct tcaactggag cagcctggcc ctcctaccca   360
agctggaagc cctggacctg gcgggaaacc agctgaaggc cctgagcaat ggcagcttgc   420
ccaacggcac ccagctccag aggctggacc tcagcggcaa cagcatcggc ttcgtggtcc   480
ccagctttt tgccctggcc gtgaggcttc gagagctcaa cctcagcgcc aacgccctca   540
agacggtgga gccctcctgg tttggttccc tggcgagtgc cctgaaagtc ctagacgtga   600
ccgccaaccc cctgcattgc gcttgcggcg caaccttcgt ggacttcttg ctggaggtgc   660
aggctgcggt gccggcctg cctagccgtg tcaagtgcgg cagacccggt cagctccagg   720
nccgcagcat cttcgcacag gacctgcgcc tctgcctgga cgaagcgctc tcctgggtct   780
gtttcagcct ctcgctgctg gctgtggccc tgagcctggc tgtgcccatg ctgcaccagc   840
tctgtggctg ggacctctgg tactgcttcc acctgtgcct ggcctggctg cccggcgggg   900
ggcggtggcg gggtgtggat gccctggcct atgacgcctt cgtggtcttc gacaaggcgc   960
agagctcggt ggcggactgg gtgtacaatg agctgcgggt acagctagag gagcgccgtg  1020
ggcgccgagc gctacgcctg tgtctggagg aacgtgactg ggtacccggc aaaaccctct  1080
ttgagaacct ctgggcctca gtttacagca gccgcaagac gctgtttgtg ctggcccgca  1140
cggacagagt cagcggcctc ctgcgtgcca gcttcctgct ggcccaacag cgcctgctgg  1200
aggaccgcaa ggacgtcgtg gtgctggtga tcctgtgccc cgacgcccac cgc         1253
```

<210> SEQ ID NO 26
<211> LENGTH: 2368
<212> TYPE: DNA
<213> ORGANISM: Canis familiaris

<400> SEQUENCE: 26

```
ggacaatgtc acgtgttttg tggacattgt gggttttggg ggctgtaacc aacctctcca    60
aggaagaggc ccctgaccag tcttcttctc tgtcctgtga ccccactggt gtctgcgatg   120
gccgctccag atctttgaac tccatgccct cagggctcac agcagctgtg agaagccttg   180
acctctccaa caatgagatc acctacattg gcaacagtga ccttcgggat gtgtgaacc   240
tcaaggctct gaggctggag tctaatggaa ttaacacaat agaggaagaa tcttttttt   300
ccctgtggag tcttgaacat ttggacttat cttataacct cttatctaac ttatcatcct   360
cctggttcag gccctttct tcattgaagt tcttaaacct actgggaaat ccttacaaat   420
cacttgggga aacacctctt ttttctcagc tcacaaatct aagaattctg aaagtaggaa   480
```

```
atatctacag cttcactgag attcaggata aggattttgc tgggctaacc tttcttgagg      540
aactggagat cgatgcttca aatctccaga ggtatgagcc aaagagtttg aaatcgattc      600
agagcatcag ctatctggcc ctccgtatga agcagcctgt tttactggtg agattttg       660 tagatctttc cagttccttg aaacatttag aactgagaga tactcatttg gacactttcc     720
acttttcaga ggcatccatc aatgaaacac atacgttggt taaaaagtgg acatttagaa     780
atgtgaaagt caccgataga agttttactg aggttgtgag actgttgaat tatgtttctg     840
gagtgttaga agtagagttt gaggactgta cccttatgg gctcggtgat tttgacatac      900
ctgatgtgga caaaattaaa aatataggtc agatagagac actaacagta cggaggttgc     960
atattccaca cttttactca ttttacgata tgagtagtat atattcactt acagaagatg    1020
ttaaaagaat cacagtagaa agcagtaagg tcttttctggt tccttgctca ctttcacaac   1080
atttaaaatc cctagaatat ttggatctca gcgacaattt agtggttgaa gaatacttga    1140
gaaactcagc ctgtcagcat gcttggcccc tcctgcaaac cttaatttta aggcaaaatc    1200
gtttgaaatc cttagagaaa actggagaaa ctttgcttac tttgaaaaac ctggtgaacc    1260
ttgatattag taagaataat tatctttcta tgcctgaaac ttgtcagtgg ccagaaaagc    1320
tgaaatgttt gaacttatcc gacacaagaa tgcaaagtat aacccgttgc atccctcaga    1380
cactggaaat tttagatgtt agcaataata atctcgagtc atttttccctg attttgccac   1440 aacttaaaga actttctatt ccagaaaata agttgaagac tctaccagat gcctccttct    1500
tacccacctt acaaattatg agaatcagca gaaacacaat aaacgctttc tcgaaggagc    1560
aactggattc ctttcacagg ctgcagaccc tggaggccgg tggcaacaac ttcctttgct    1620
cctgtgaatt cctgtctttc actcaggagc agcaggccct ggccgggctc ctggtcggct    1680
ggccagagga ctacctgtgc cactcccct cctacgtgcg gggccagcgg gttgggaccg    1740
cccggctccc ggcttctgag tgccaccgga cagctctggt ggccgccgtg tgctgtgtct    1800
tgctcctgct ggtcctgctc acggcggggg cgtgccacca tttccacggg ctgtggtacc    1860
tgagaatgct gtgggcctgg ctccaggcca aaggaagcc caggaaagcc cctccaggg     1920 acgtctgtta tgacgccttt gtgtcttaca gtgagcatga ttcctactgg gtggagaacc    1980
ttctggtcca gaagctggag cacttcaatc ccccgttcaa gttgtgcctt cacaagcggg    2040
actttattcc cggcaagtgg attattgaca atatcattga ctccatcgag aagagccaca    2100
aaaccatctt tgtgctttct gaaaacttcg tgaaagcga gtggtgcaag tacgagctgg    2160
acttctccca ttttcgcctc tttgatgaga caacgatgc tgccatcctc attcttctgg    2220
agcccattga gaaaaggcc atcccccagc gattctgtaa gctgcggaag ataatgaaca    2280
ccaagacgta cctggagtgg cccaccgatg atgctcagca ggaagggttt tggttaaatt    2340
tgagaacagc aataaaatcc tagattcg                                       2368
```

<210> SEQ ID NO 27
<211> LENGTH: 2709
<212> TYPE: DNA
<213> ORGANISM: Canis familiaris

<400> SEQUENCE: 27

```
aaaaactaac atctctagag gatttcccca ttggacatct caaaaccttg aaggagctta      60
atgtggctca caatcaccat tccttcaagc cacctgcgta tttctctaac atgcccaacc     120
tggagaacgt ggtatctttc caataacaag atccaaaata tttatcgtga agacttgcag     180
```

-continued

```
gatatctgca tcacatgcca ctactcaacc tttctttaga cttgtccctg aacccttat      240 actttatcca accaggttcc tttaaagaaa ttaaactcca taaactgact ttgagaagta      300
attttaatag tacagatgta atgaaaactt ttattcaaag tctggctggc ttaaagatca      360
atcagttggt tctgggagaa tttaaaaatg aaaggaagtt ggaaagcttt gacaattctc      420
tcctggaagg actgtgcaat tgaccattg aaaaattccg datagcatac tttgatagct       480
tctcaaagga tactactaac ttatttaacc agttggtaaa catttctgca atttctttgg      540
cgcatctgta tttagacaca ccaaaatacc ttcctaaaaa tctcagatgg caacggttgg      600
aaatagttaa ttgtaactta gaacaatttc ccgcatggga gctggactct ctcaaggagt      660 tgttctcac ttccaacaaa ggtatgaaca cttttgctga tatgaagatg gaaagccttg       720
agtttctaga tctcagtaga aatcgcctga gtttcaagac ttgctgctct cactctgatt      780
ttgggacaac cagactgaag catttagatc tgagcttcaa tgaaatcatt accatgagtt      840
caaacttctt gggcttagaa caactggaat atctagattt acagcattcc agtttgaagc     900
aggccagtga tttttcagta ttcttgtccc tcagaaacct ccgttacctt gatatttctt     960
atactcgcac tgaagttgct ttccagggca tttttgatgg cttggtcagc ctcgaagtct    1020
tgaaaatggc tgataattcc tttccggaca actcccttcc aaatatttac aaagggttga    1080
ctaacttaac cattctggac cttttctaggt gtcatctgga acgggtgtcc caggaatcat    1140
ttgtctcact tcctaaactt caggtgataa atatgagtca caatagcctc ttgtcattgg    1200
atacactagc ttatgaacct ctcctctccc tccagatcct agattgcagt ttcaatcgaa    1260
tagtagcctt caaggaacaa ggacaacagc attttccaag taatctagtt tccttaaatc    1320
ttactcggaa tagctttgct tgtgactgtg aacatcagag tttcctgcag tgggtcaaag    1380
accacaggca gctcttggtg aaagttgaac aaatggtgtg tgcaaaacct ttagacatga    1440
aggacatgcc cttgctaagt tttaggaatg ccaccctgtc agaggaagca agactatcaa    1500
ttagtgtgtc agttttcact gtgcttcatg gtttctctgg tagcagtttt agccggtata    1560
agttctattt tcacctgatg cttctcgctt ggcttgcaaa aggtataaca gaggggaaag    1620
tacctatgat gcattttgtt atctactcaa gccaggatga agactgggtg aggaatgaat    1680
tggtaaagaa cttggaggag ggagtgcccc cctttcagct ctgccttcac tacagagact    1740
tcattcctgg tgtggccatc gccgccaaca tcatccagga aggcttctac aaaagccgga    1800
aggttattgt tgtggtgtcc caacacttca tccagagtcg atggtgcatc tttgagtatg    1860
agattgccca gacttggcag tttcttagca gtcgtgctgg catcatcttc attgtcctgc    1920
agaaggtgga gaagtccctg ctgcggcagc aggtggaact gtatcgcctc ctcagcagga    1980
acacttacct ggaatgggaa gacagtgtcc tggggcgcca catcttctgg agacggctcc    2040
gaaaagcctt gctggatggt aaaccgtgga gtccagaagg aacagaggat gcagaaaaaa    2100
gctagcatga agcaggaaac tctgcttgag gatgaaaagc tcctgtggtg cttcttgccc    2160
agctggaccc agtacttgtt cagttagcga tgtacctgcc actgtgctaa gggcggatga    2220
ttcagtggtg cacgagggct gcaggatgcc aacctcatgg agtttacagt gcagagggaa    2280
taaagctgtg ctaaaccaca gaacctccag gtggatgctt ccaccaaatc agctgaggag    2340
tccatggctg agtccatgga aagtcaactc aattcttacc ccatcaaact gagttggaac    2400
taggagactg gtcccagag agatcaggga agagatatag ttcttcaact gagtctctgg    2460
agtggaaact acctcatgac atgctagctc tctgaaagct gtttgggcag ttttaactga    2520
accaggtctt tgcccacttt tcccttttct attgaatgca attgaaattc cgcttgatga    2580
```

```
ctcaaaagga tcctgattca gatcccttcc ccactactct aagccagttt ccttacaaag    2640
gctaaataaa gtctagcaac tagttccaaa ggaattctga ttaacgcaaa aaaaaaaaaa    2700
aaaaaaaaa                                                            2709
```

<210> SEQ ID NO 28
<211> LENGTH: 4244
<212> TYPE: DNA
<213> ORGANISM: Canis familiaris

<400> SEQUENCE: 28

```
aaacccctga accaccgagg tccccacagc ccctctgctc tgctctcttc aaccagactt      60
ctgtatttca cggtggaaga agactaaaaa tggtgtttcc aatgtggaca ttgaagagac     120
agttctttat ccttttgaac ataatcctga tttccaaact ccttggagcc agatggtttc     180
ctaaaactct gccctgtgat gtcagcctgg atgctccgaa ggcccatgtg attgtggact     240
gcacggacaa gcacctgacg gaaatcccgg gaggtattcc ctccaacgcc accaacctca     300
ccctcaccat taaccacata cccggcatct ctccagcctc cttccaccag ctggactatc     360
tggtagagat cgatttccga tgcaactgta tacctgttcg actggggccg aaagaccatc     420
tgtgcaccag gaggccacag attaaaccca gaagctttag cagcctcact tatttgaaat     480 cccttatct ggatggaaac cagcttctag aaatacccga gggtcttcct cccagcttgg      540
agctgctgag cctcgaagcc aacagtatct tctctatcat gaaatataac ctaacagaac     600
tgaccaacat agaaaggctc tacttgggcc aaaactgtta ttttcgcaat ccttgtaatg     660
tttcattttt catcgaaaaa gatgctttcc taagtctgaa aaatctaaaa ttgctctccc     720
tcaaagataa caacatcacg tatgtcccta ctactttgcc gtctacttta acagaactct     780
acctttataa caacgccatt gcaaaaatcc aagaagatga ttttaataac ctcaatcaac     840
tgcgcatact cgacctaagt ggaaattgcc ctcgttgtta caatgtccca tttccttgca     900 cacccctgtga aaataattcg cccctacaga tccatgagtc agctttcgat gcattgacag     960
aattacaggt gttacgtcta cacagtaact ctcttcagcg tgtgccccag agatggttta    1020
aaaacattaa aaagctcaag gagctcgatc tgtcccaaaa cttcttggcc aaagaaattg    1080
gggatgccaa attttttgtat cttcttcacg accttgtcca actggatcta tctttcaatt    1140
atgaacttca ggtctatcgt gcagctctga atctgtccga cgcgttttct tcactgaaaa    1200
acctgaaagt gttgcgcatc aaaggatacg tctttaagga gctgagcagc catcatctct    1260
ctccgttaca gagccttacc aatctcgaag ttcttgatct cggcactaac ttcataaaaa    1320
ttgcggacct cagcatattt gaacaattta aaacactgaa agtcatagac ctttcgatga    1380
ataagatatc cccttcagga gattcaggtg aagttggctt ctgctctagc accagaacct    1440
ctgtcgaagg tcatgcgcct caggtccttg agacattaca ttatttcaga tatgacgagt    1500
atgcaaggag ttgcaggttc aaaaacaaag agactccttc tttcttgcct tttaacaaag    1560
attgttacat gtatgggcag accctggacc taagtagaaa caacatcttt tttatcaagt    1620
cctctgattt tcagcatcct tctttcctca aatgcctaaa tttgtcagga aataccattg    1680
gccaaactct caatggcagt gaatttcagc cactagtgga gctgaaatac ttggacttct    1740
ctaacaaccg gcttgattta ctctactcga cggcatttga ggagctacgc aaactggaag    1800
ttctagatat tagcagtaac agccattact tcaatcaga aggaatcact cacatgctaa     1860
acttcaccaa gaacctaaaa gttctgaaga aactgatgat gaacaacaat gacatcgcta    1920
```

```
cgtccaccag caggaccatg gagagtgagt ctcttaaaat tctggaattc agaggaaatc    1980
atttggatgt tttatggaga gatggtgata acagatactt aaagttcttc aagaatctgc    2040
tgaacttaga ggaattagac atctctgaaa attccctgag cttcttgcct tctggagtgt    2100
ttgatggcat gcctccgaat ctaaagactc tctccttggt caaaaatggg ctcaagtcct    2160
ttcactggga aagactccag tatctgaaga atctagagac tttggacctc agctacaatg    2220
agctgaagat tgtccctgag agattataca actgttccag aagcctcaag aagctgattc    2280
ttaagtataa tcaaatcagg cagctgacaa agcattttct acaagatgct ttccagttgc    2340
gatatctgga cctcagctca aataaaatcc agattatcca agactagc tttccagaaa     2400
atgtcctcaa caacctggag atgttacttt tgcatcataa ccggtttctg tgcacctgtg    2460
atgctgtgtg gtttgtctgg tgggtcaacc acacagaggt gactattcct tacttggcca    2520
cagatgtgac ttgtgtgggg ccaggagcac acaagggcca gagtgtggtc tccctggatc    2580
tgtatacctg tgagttagat ctgactaacc tggttctgtt ctcattttcc ctatcgctgg    2640
ccctttttct gatggtgatt acaacagcaa accacctcta cttctgggac gtgtggtaca    2700
gttaccatta ctgtaaggcc aaaataaagg ggtatcggcg tctgaaatca ctggactctt    2760
gctatgatgc tttcgttgtg tatgacacta agacccagc agtgaccgaa tgggttttgg     2820
atgagctggt ggccaagctg aagaccccaa gggagaaaca tttcaattta tgtcttgagg    2880
aaagggattg gttaccaggg cagccagttc tggaaaacct ttcccagagc atacagctta    2940
gcaaaaagac ggtgtttgtg atgacgaaca gtatgcaaa gaccgagaac tttaagatag     3000
cattttactt gtcccatcag aggctcatgg atgaaaagt ggacgtcatt atcttgatat      3060
tccttgagaa gcccctttcag aaatccaagt tcctccagct ccgcaagagg ctctgtaaga   3120
gttctgtcct ggagtggcca agaaacccac aggctcaccc atacttctgg cagtgcctga    3180
aaaatgccct ggccacagac aatcatgtga cctacagcca ggtgttcaaa gagacggtct    3240
aggccttctt tgcaaaatgg ggctgcctga ctcaccaagg agaagcttgg ctgcctagat    3300
tttctcttcg atgtctcact agaagggtgc tcgtaaattc tctaagaccc gggatggccc    3360
atagcagaga ggctggtgga agttggaaaa tggaatttat atgatacatc gagtcatctt    3420
acttatctct ctgtgactcc atttgcactg gagcctctcc tctctgttcc tggatagatg    3480
ctattgggag gacggcggca aggagaggac acgaggctct gactctcctg taatcctcta    3540
gtgattatta aatagacgtg caatcacaga ctactgagaa gaattgcact tcttcccgaa    3600
gaagaactac tggtatgtgt caaaaacgct cggggcctgc gtacaggaca ttaaaatgta    3660
gcagagtttg tgaaatgaaa acccagtcaa ctcgtcacct gatggcttct ttctgtgcag    3720
acccagagct ggctccccac ggaggattgc ctacgtgcca ctgtctcttc gcccttgggc    3780
ctgttgctgg gtccctggtg aaatagtga gaaacaccct taccactggt gggcttggcc     3840
tacttacaaa tggaaaaaaa ttgaagctga tctgccttta tacaaatgag gctctttacc    3900
cttgatgata actcacctgc tcaagtattg ttacggactg aacgtctgtt ccctcccaaa    3960
ttcagatgtt gaagtgccaa ctcccagtgg gatggtgtca ggaggtggcc tttgggggg     4020
tgatcaggcc acgagggtgg agcctgcagg aatgggatca gtgctttatc agaagatagc    4080
agagggacgc cagggtggct caggggttga gcatctgcct ttggcccagg gcgtgatccc    4140
ggggtcccag gatggagtcc cgcttcgggc tccccgcagg gagcccgcct ctccctctgc    4200
ccgtgtctct gcctctctct gtgtctctca tgaacaaata aata                     4244
```

<210> SEQ ID NO 29
<211> LENGTH: 2931
<212> TYPE: DNA
<213> ORGANISM: Canis familiaris

<400> SEQUENCE: 29

| | | | | | |
|---|---|---|---|---|---|
| atggggttca | gtgagggatg | tggaggtggg | ggtgggtcct | cgctgctccg | ggtgggccct | 60 |
| gccaccatca | cgagggtctt | cacgagctgg | gggctgcagg | gtcggctgga | gagggtggat | 120 |
| gaagcgtcgg | ggccacgcgg | cctggcgggc | cttgcctccc | tgggtgcgtc | cgaggccgca | 180 |
| cagtcctgct | gctcctgtca | agggccggcg | cccgtgctcc | agcttgggga | tggggagtgg | 240 |
| gtccctggc | cagctccctg | gtccctcgtg | agtgaccctg | gggggccctc | gggctctcga | 300 |
| gccatcagcg | tcatcatccg | agaccagctc | ccacgatctg | gagcaaagat | tttgttcgcg | 360 |
| acccgccgcg | cccggatctc | agatctccgc | gccctggcgc | tcctggttcg | cgcctccccc | 420 |
| agcgctgcgc | tccccagcca | ggtggccccg | tggatcgatc | tctcatccat | tatccccccc | 480 |
| aactgcaccg | tgagctctgc | aaggactgaa | gacctgtgcg | tcgtgggcca | caacagcacc | 540 |
| tgcaacagct | ctttgcacat | ggtaggtcct | ccacgaatat | ttgcccagcg | cattgcgaga | 600 |
| ggaggagagg | aaggagtggg | cgttctgttc | acaaacgacg | aacccgacct | aagtgggttc | 660 |
| cacaggctgg | caggggcaga | gcgaggcccc | caccccgtgg | gtgcttccat | cccaccaggt | 720 |
| gcccgctgtg | cagggtgcgc | agtggacttt | ggccaggagg | ccttggacgg | gggtgcagaa | 780 |
| tgcaacccgg | caggtctgcc | gcagcatccc | ccatgggact | cggtatggct | gcacctacct | 840 |
| gtgcccatgg | cctgcgcgga | cctgtcgctc | tccagcgcct | ttgacattct | aggtgccgca | 900 |
| ggccaggaca | agctcttgcg | tcttaagcac | aagctaaaga | ccctgcgcct | gggctgccgg | 960 |
| ggggcagacc | tcctgcacgc | catggtgctc | ctgaagctgg | gccgggagac | ggaggccagg | 1020 |
| atctccctgg | aagcactgaa | ggcggacgcg | gtggcccggc | ttgtggcgca | ccagtgggcc | 1080 |
| ggcatggatg | gtgccgaggc | ccccaaggag | ccaccagact | tgtcctgggc | agttgcccgg | 1140 |
| gtgtaccacc | tgcttaccga | ggagaacctg | tgcccggcca | cgatgcggga | cctggcctac | 1200 |
| caggcggccc | tccggacctt | cagctctagg | gatgaccacc | ggctggccga | gctccaggga | 1260 |
| gaggcccggg | accggtgtgg | gtggggcatc | gtcgggaccc | cggggagctt | ccagccccctt | 1320 |
| cactccgatc | tgggctgcct | cccagcatcc | tcagtgtcac | cctcaggcgc | ccgcagcctt | 1380 |
| ccaaagccca | tagaggaccc | ctcggcctgg | agccgaggcc | gttccctgag | atccaccggc | 1440 |
| agcccagcct | ccctggccag | caatctggaa | atcagcgagt | cgcccaccat | gccctttctc | 1500 |
| agccgtcacc | gcagctgcca | tgaacccagc | aagctgtgcg | acgagcccca | ggccagcctg | 1560 |
| gtgcccgagc | ctgcccccac | gggctgccag | gagcctgagg | aggtgagctg | gccaccatca | 1620 |
| gaagagactg | ccagcccccc | accagaggag | acggccatcc | ccacgccgcc | tcctgacgtg | 1680 |
| gtcccagatg | caagcctcag | tgaccagctc | gacccccca | aagcggggca | gatgggcacc | 1740 |
| cactaccccg | tggaatgcac | tgaaatgttg | cagcccccca | gctctctgtc | cttgccctct | 1800 |
| ggaaatgctc | gccctgtcaa | ggaccagacc | ccactccac | ttcctgtaga | agacaccgct | 1860 |
| tcccagttgc | caaccccag | cccacctcct | ccctcagccc | tgaggacgtc | ccctccctgc | 1920 |
| ccttttccat | ccacctctcc | ttccactggc | ccggtcccct | cgcacccctg | tccaccttct | 1980 |
| ccaaattctc | ccgaattgga | gtcggaacag | aaattctata | actttgtgat | cctgcacgcg | 2040 |
| gcggcggacg | agcacatcgc | cctgcgggtc | cgggagcggc | tggaggccct | gggcgtcccc | 2100 |
| gacggtgcca | ccttctgcga | ggacttccag | gtgcccgggc | ggggcgagct | gcgctgcctg | 2160 |

| | |
|---|---:|
| caggacgcca tcaaccactc ggccttcacc atcctgctgc tcaccccaa cctcaactgc | 2220 |
| cgcctgggcc tgcatcaggt gagccagtcg ctgatgagca gcctcacgcg cacgggtgg | 2280 |
| caagactgcg tgatccccttt cctgcccctg gagagctccc aggcccagct cagccgggac | 2340 |
| acgtgcagcc tgctcagcag cctggtgtgg ctggacgagc actcccgggt cttcgccagg | 2400 |
| agggtggtca acacgttcaa ggcgcagcag ctgcgagccc gcaaggccca gtggaagaag | 2460 |
| gaacaggaca tccgggccct gcagcagcag cgccagcacc tggagggtga gcggcagcag | 2520 |
| gtggcctcgc tgagcgccgc ctactccgcc tacctccaga gctgctcgtc gtggcaggcg | 2580 |
| cagatggagg cgctccgggc ggccttcggg agccacatgc catttggggc tcaggggccc | 2640 |
| tacgggggcc cggggcctct gggggccccc ccgcccctcc cctcctggtt gggccaccag | 2700 |
| cctcccgccg cgccgccgtg gctggccggc tcgcccgcgc ccgccttccc gcccgcgccc | 2760 |
| gccttcccgc agcccccgc cttctcgccg ccccccgcgc ccccgcagag cccggggctg | 2820 |
| cagccctca tcatccacca cgcgcagatg gtgcagctgg gcgtcaacaa ccacatgtgg | 2880 |
| aaccagcgag ggacccaggc gcccgaggac gagacgcaag gagcagagtg a | 2931 |

<210> SEQ ID NO 30
<211> LENGTH: 2370
<212> TYPE: DNA
<213> ORGANISM: Canis familiaris

<400> SEQUENCE: 30

| | |
|---|---:|
| atgaaaacta atcctagcat cttccaattt gccatcatct tcatattaat acttgagatc | 60 |
| agaatacaat tgtctgaaga agtgattttt ctagttaaca gatcaaaagc aggtctcttt | 120 |
| cacattccca agacctatc cctgaaaaca acaatcttag atatatcaca aaactatata | 180 |
| tctgagcttc agacttctga catcctatca ctatcaaagc tgaggatttt gattgtttct | 240 |
| tataatagaa ttcaatatct tgatatcagt gttttcaaat tcaaccagga attggaatac | 300 |
| ttggatctgt cccacaatga gttggggagg atttcttgcc atcctaccgt gaaccctcaag | 360 |
| cacttagacc tttcatttaa tgcatttgat gatctaccca tatgcaaaga gtttggcaac | 420 |
| atgtctcaac tagagtttct ggggttgagt gccacacagt tacagaaatc tagcatgcta | 480 |
| ccaattgctt ctttgcatat cagaaaggtt ttactggtct taggagacac ttatgggaaa | 540 |
| aaagaagacc ctgagagcct tcaaaagctt aacacagaaa gtcttcacat tgttttccct | 600 |
| ataagaaagg aattcagttt tactctggat gtatcagtca gcactgcagt aagtctcgaa | 660 |
| ttgtctaata tcaaatgtgt gccagatggt catggatggt cttatttcca aaatgttctg | 720 |
| tcaaaacttc aaaagaattc aaggttatca agtcttactt taaacaacat tgaaacaact | 780 |
| tggaattttt tcattatgct ccttcagttg gtttggcata caagcataga gtatttctca | 840 |
| atttcaaatg taaaactaca aggttaccct gacttcagag attttgatta ttctgacact | 900 |
| tcactgaagg cctatctat acaccaagtc gttagtaatg cattcaattt gccacaaagt | 960 |
| tatatctata aaatcttttc aaatatgaac atccaaaatt tcacagtgtc tggtacgcac | 1020 |
| atggtccaca tggtttgccc atctcaaatt agtccatttc tgcatttgga ttttctaat | 1080 |
| aatctcttaa cagacattgt ttttaaaaat tgtagaaact tgattaaact ggagacactt | 1140 |
| agtttacaaa tgaatcaatt aaaagaactt gcaagtatag ctcaaatgac caacgagatg | 1200 |
| aagtctctac aacaattgga tattagccag aattctctaa ggtatgatga aaatgaagga | 1260 |
| aactgctctt ggactagaag tttattaagt ttaaatatgt cttcaaatat acttactgac | 1320 |
| tctgttttca gatgtttacc tcccaaggtc aaggtgcttg atcttcacga taacagaata | 1380 |

```
aggagcattc ctaaaccaat catgaagcta gaagatttgc aagaactcaa tgttgcttcc    1440
aattctttag cccactttcc tgactgtggt acttttaata ggctttctgt actgatcatt    1500
gactctaatt caatttccaa tccatcagct gatttcctcc agagctgcca taacattagg    1560
tccataagcg cagggaataa tccattccag tgtacatgtg agctgagaga atttgtccaa    1620
agtctaggcc aggtagcaag caaagtagta gagggttggc ctgattctta taagtgtgac    1680
tctccagaaa actataaggg aaccctactg aaggactttc acgtgtctcc gttatcctgc    1740
aacacaactc tgctgcttgt caccattggg gtcgctgtgc tagtgttcac tgttactgtg    1800
actgcgctct gtatctactt tgatctgccc tggtatctta ggatggtgtt tcagtggacc    1860
cagacccggc gcagggcaag aaacacaccc ttagaaaatc tccaaagaac catccagttc    1920
catgctttta tttcatatag cgggcatgat tctgcctggg tgaagagtga attactacca    1980
aacctagaaa agaagaact aaggatttgt ctccatgaga gaaactttat tcctggcaag    2040
agcattgtgg aaaatatcat aaactgcatt gagaaaagtt acaagtccat ctttgttctg    2100
tctcccaact ttgttcagag tgagtggtgc cattatgaac tgtactttgc ccaccacaat    2160
ctctttcatg aaggatctaa taacttaatc ttgatcttgc tggaacctat tccacagtat    2220
tccattccta gcagctatca caagctcaaa aatctcatgg cacaaaggac ttatttggaa    2280
tggcccaagg agaagagcaa acatggactt ttttgggcta acctaagagc gtctattaat    2340
attaaattga gggagcaagc aaaaaaatag                                     2370

<210> SEQ ID NO 31
<211> LENGTH: 1155
<212> TYPE: DNA
<213> ORGANISM: Canis familiaris

<400> SEQUENCE: 31
gcgaagacgg cgctgcggtc cccggcgtcc ggccatggcc gccgagggct cccgcgcggg      60
gtccgcctcc ccggtctgcc ccaaggcttc cctgccctg gctgctctca acgtgcgagt     120
gcgccgccgc ctgtctctgt tcctgaacgt gcgcacgcag gtggcggccg actggaccgc     180
gctggccgag gagatgggct tcgagtacct ggagatccgg cacctggaga tgcacgccga     240
ccccacgggc aagctgctgg acgactggca gggacgccct ggcgcctcgg tgggccgcct     300
gcttgagctg ctcaccaagc tgggccgaga cgacgtgttg gtggaactgg ggcccagcat     360
cgaggaggat tgccaaaagt atattctgaa acagcagcag gaggagtctg agaagccctt     420
acaggtgcct gctgttgaca gcagtgaccc acggacacca gagcgagggg gcatcaccat     480
gcttgatgat ccctcagggc aaatgcctga gcgttttgat gccttcatct gctactgccc     540
cagcgatatc cagtttgttc aggaaatgat ccggcagctg aacagacaa actatcggct     600 gaagttgtgt gtgtctgatc gtgatgtctt gcctggcacc tgtgtctggt ccattgccag     660
cgagctcatt gagaagaggt gccgccggat ggtagtggt gtctctgatg attacctgca     720
aagcagggaa tgtgacttcc agactaagtt tgcactcagt ctctctccag gtgcccatca     780
gaagcgactg atccccatca agtacaaggc aatgaagaaa gagttcccca gcatcctgcg     840
gttcatcact gtctgtgact acaccaaccc ctgcaccaag tcctggttct ggactcgcct     900
cgccaaggcc ctgtccctgc cctgaagact gccctgggac cgtgggtggg tgtgtgtcta     960
tctctcagcc tctgcgtgca cttctgcccc tgcttcctcc tgcagtggtt gggtaagct    1020 gtgctccact tgcctcttca ttcctggaga tgccaactct gcagacatct gtagccactg    1080
```

```
tacctagctg ggacatggca tgtcatgtcc tttgtggaac cagtagctat taagtggcat    1140
gtccacatgc taggt                                                     1155
```

PATTERN RECOGNITION RECEPTOR EXPRESSION AS A MEASURE OF SYSTEMIC HEALTH

SEQUENCE LISTING

The instant application contains a Sequence Listing which has been submitted via EFS Web and is hereby incorporated by reference in its entirety. Said ASCII copy, created on Dec. 19, 2012, is named 9897-00-WO-HL_Sequence_Listing_ST25US.txt and is 49000 bytes in size

BACKGROUND OF THE INVENTION

Humans and non-human mammals, including companion animals are susceptible to periodontal disease and other afflictions and conditions of the oral cavity. Periodontal disease develops, in part, as a consequence of the adherence of plaque, a mixture of oral bacteria and saliva components, to the surface of the teeth. This adherent plaque hardens to form tartar (calculus), which can lead to inflammation, swelling, and infection of the gums. There have been suggestions in the art that there might, in some instances, be a correlation between such diseases of the teeth and gums and other systemic diseases, including cardiac conditions. In a similar vein, there has also been speculation in the art that maintaining the teeth and gums of an animal might decrease the rate of mortality and extend the life span of that animal.

However, there do not appear to be any studies in the art that actually demonstrate the relationship of (a) oral health, (b) pattern recognition receptor expression levels, and (c) the beneficial effect of therapy of oral health conditions on systemic disease outcomes.

Accordingly, there is a need for studies that would establish whether or not there is a causal link between oral health conditions and the overall systemic health of the animal. In addition, if that causal link were to be established, then there would develop a need for a rapid, facile, accurate, and sensitive method for evaluating systemic health in subjects, particularly in companion animals, afflicted with an oral health condition.

BRIEF SUMMARY OF THE INVENTION

The present invention is directed to a method for measuring systemic health in a subject in need thereof, where the subject is afflicted with an oral health condition. The method comprises determining the expression level of at least one pattern recognition receptor in the subject, and then comparing that level of expression to a control. In one aspect of the invention, the control is a baseline control corresponding to the measured baseline level of expression of that same pattern recognition receptor (or those same pattern recognition receptors) in the afflicted animal before therapy. A healthy control level would be the level of expression in the same animal when the oral cavity is brought to a state of good oral health through intervention (complete dental prophylaxis) or good oral hygiene. In other aspects, the healthy control can be the measured level of expression of that same pattern recognition receptor (or those same pattern recognition receptors) in healthy control animals that are not afflicted with the oral health condition. According to the method, poor systemic health in an animal with an oral care condition, as it relates to the effect of oral health on systemic health, is indicated where the pattern recognition receptor expression levels measured in the tested subject are greater than those of the healthy control.

In certain embodiments, of this method, the pattern recognition receptor is selected from the group consisting of Toll Like Receptor 1 (TLR1), Toll Like Receptor 3 (TLR3), Toll Like Receptor 4 (TLR4), Toll Like Receptor 7 (TLR7), Toll Like Receptor 9 (TLR9), Toll Like Receptor 10 (TLR10), myeloid differentiation primary response gene 88 (MyD88), and Nucleotide Binding oligomerization domain containing protein 1 (NOD1).

In another embodiment, the method of the invention comprising determining an expression level of at least one second pattern recognition receptor in the subject afflicted with an oral health condition, comparing that level of expression to a control. Again, the baseline control level of expression can be that of the same afflicted animal (the expression level before treatment of the oral health condition), while the healthy control can be the level of expression determined for the same second pattern recognition receptor in healthy control animals not afflicted with the oral health condition. Good systemic health, i.e., as it relates to the effect of oral health on systemic health, is indicated where the expression level of the pattern recognition receptor measured in the tested subject is equal to or less than that of the healthy control, and poor systemic health (as it relates to the effect of oral health) is indicated where the expression level of the second pattern recognition receptor measured in the tested subject is greater than that of the healthy control. In particular aspects of this embodiment, the at least one second pattern recognition receptor is selected from the group consisting of Toll Like Receptor 1 (TLR1), Toll Like Receptor 3 (TLR3), Toll Like Receptor 4 (TLR4), Toll Like Receptor 7 (TLR7), Toll Like Receptor 9 (TLR9), Toll Like Receptor 10 (TLR10), myeloid differentiation primary response gene 88 (MyD88), and Nucleotide Binding oligomerization domain containing protein 1 (NOD1).

In certain embodiments, wherein the subject is a companion animal, and in particular aspects of this embodiment, the companion animal is a feline or the companion animal is a canine.

In certain embodiments of the methods of the invention, the oral care condition of the subject to be treated comprises periodontal disease. In particular aspects of these embodiments, the periodontal disease may comprise one or more of gingivitis, periodontitis, dental plaque, dental tartar, resorptive tooth lesion, mobile tooth, attachment loss, and gingival recession.

The present invention is further directed to a method for determining the efficacy of treatment of an oral health condition in an animal in need thereof and/or for monitoring the efficacy of a treatment on the systemic health of an animal in need thereof, where that animal is afflicted with an oral health condition, and wherein the treatment comprises treatment or therapy of the oral health condition. This method comprises (a) determining the expression level of a first pattern recognition receptor in the animal at a first time point prior to or shortly after the treatment, (b) determining the expression level of the same pattern recognition receptor in the animal at a second time point subsequent to the first time point, and (c) comparing the expression levels measured at the two time points. According to this method, efficacy of the treatments is indicated where the expression level at the later time point is lower than that measured at the first time point. In another aspect of this method the level of expression of two or more pattern recognition receptors may be measured and compared at each time point. In certain aspects of these embodiments, the first time point may be a month, three weeks, two weeks, one week or less prior to the treatment. In other aspects of these embodiments, the first time point is taken less than a day before the treatment. In still another aspect, the first time point is taken less than a day after the treatment.

The present invention is also directed to a method for diagnosing a systemic health condition in a subject in need thereof, where the subject is an animal afflicted with an oral care condition. This method comprises determining the expression level of a first pattern recognition receptor in the subject comparing it to a control value. In one aspect of the invention, the control is a baseline control corresponding to the measured baseline level of expression of that same pattern recognition receptor (or those same pattern recognition receptors) in the afflicted animal before therapy. In another aspect, the control value is a healthy control level corresponding to the level of expression in the same animal after the oral cavity is brought to a state of good oral health through intervention (complete dental prophylaxis) or good oral hygiene. In another aspect, the healthy control can be measured as the level of expression of that same pattern recognition receptor (or those same pattern recognition receptors) in healthy control animals that are not afflicted with the oral health condition. According to the method, poor systemic health in an animal with an oral care condition, as it relates to the effect of oral health on systemic health, is indicated where the pattern recognition receptor expression levels measured in the tested subject are greater than those of the healthy controls.

The present invention is also directed to a method for treating a chronic systemic inflammation in an animal in need thereof and afflicted with an oral health condition. The method comprises subjecting the animal to a dental prophylaxis treatment designed to ameliorate periodontal disease in the subject animal in need thereof.

In a particular aspect of the present invention, the pattern recognition receptor or receptors, the expression levels of which are measured in the above-described methods of the invention, are selected from the group consisting of Toll Like Receptor 1 (TLR1), Toll Like Receptor 3 (TLR3), Toll Like Receptor 4 (TLR4), Toll Like Receptor 7 (TLR7), Toll Like Receptor 9 (TLR9), Toll Like Receptor 10 (TLR10), myeloid differentiation primary response gene 88 (MyD88), and Nucleotide Binding oligomerization domain containing protein 1 (NOD1), and the oral health condition of the indicated subjects and animals indicates the presence of periodontal disease.

In addition, in particular aspects of these embodiments, the subject or animal afflicted with and oral health condition is a companion animal, e.g., canine or feline companion animal, such as a dog or a cat.

The present invention also encompasses kits useful for practice of the methods described herein. In one embodiment, the present invention includes a kit for determining the expression level of a feline pattern recognition receptor, where that kit comprises forward and reverse primers suitable for polymerase chain reaction amplification of cDNA corresponding to at least one pattern recognition receptor selected from the group consisting of feline Toll Like Receptor 1 (TLR1), feline Toll Like Receptor 3 (TLR3), feline Toll Like Receptor 4 (TLR4), feline Toll Like Receptor 7 (TLR7), feline Toll Like Receptor 9 (TLR9), feline Toll Like Receptor 10 (TLR10), feline myeloid differentiation primary response gene 88 (MyD88), and feline Nucleotide Binding oligomerization domain containing protein 1 (NOD1).

In another embodiment, the present invention includes a kit for determining the expression level of a canine pattern recognition receptor, where that kit comprises forward and reverse primers suitable for polymerase chain reaction amplification of cDNA corresponding to at least one pattern recognition receptor selected from the group consisting of canine Toll Like Receptor 1 (TLR1), canine Toll Like Receptor 3 (TLR3), canine Toll Like Receptor 4 (TLR4), canine Toll Like Receptor 7 (TLR7), canine Toll Like Receptor 9 (TLR9), feline Toll Like Receptor 10 (TLR10), canine myeloid differentiation primary response gene 88 (MyD88), and canine Nucleotide Binding oligomerization domain containing protein 1 (NOD1).

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

The following description of the preferred embodiment(s) is merely exemplary in nature and is in no way intended to limit the invention, its application, or uses.

As demonstrated herein, the present inventors have discovered that there is a systemic response to poor oral health and there is a causal connection between oral health and systemic health. The presently-described invention, which is based in part on this discovery, encompasses measuring systemic health in a subject in need thereof, where the subject is afflicted with an oral health condition. The methods described herein comprise determining the expression level of at least one pattern recognition receptor in the subject, and then comparing that level expression to a control, where increases in the expression levels of pattern recognition receptors is indicative of poor or declining systemic health in the subject afflicted with an oral health condition.

Definitions

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are now described. All publications mentioned herein are incorporated by reference for the purpose of describing and disclosing the materials and methodologies that are reported in the publication, which might be used in connection with the invention.

As used herein and in the appended claims, the singular forms "a", "an", and "the" include plural reference unless the context clearly dictates otherwise.

As used herein, the term "animal" is a human, a non-human animal, or a non-human mammal, where the term non-human animal includes non-human primates (e.g., monkeys, chimpanzees, apes etc.), companion animals and house pets (e.g., dogs, cats, rabbits etc.), laboratory animals, domesticated animals, livestock and farm animals (e.g., horses, goats, sheep, swine, llamas, alpacas, bovine animals etc.). In one embodiment, the animal is a non-primate mammal. In another embodiment, the animal is a non-human primate. In a specific embodiment, the animal is a domesticated companion animal or "house" pet, such as canine or a feline. In one aspect, the animal is a dog. In another aspect the animal is a cat.

As used herein, "oral care condition" is any disorder or condition of the oral cavity, including disorders or conditions of the teeth, oral mucosa, gingiva and tongue. Such conditions include periodontal disease, which may encompass, without limitation, one or more of gingivitis, periodontitis, dental plaque, dental tartar, resorptive tooth lesion, gingival recession, gingival attachment loss, mobile tooth, and combinations thereof.

According to the invention, the phrase "animal in need thereof," refers to a human or a non-human animal for whom or for which treatment is required for an oral care condition including, but not limited to, periodontal disease, which may encompass, without limitation, one or more of gingivitis, periodontitis, dental plaque, dental tartar, resorptive tooth lesion, gingival recession, gingival attachment loss, mobile tooth, and combinations thereof.

The term "treating," as used herein, means to cure, inhibit, ameliorate, or arrest the development, relieve the symptoms or effects of, or to ameliorate, or cause the reduction in the symptoms or effects of an oral care condition in an animal in need of treatment for that condition. Accordingly, it should be recognized that the terms "ameliorating," "treating," and "controlling," are not intended to limit the scope of the invention and that, although distinguishable from one another, there can be overlap amongst these terms.

The term "companion animal" used in the present invention includes any non-human animal suitable for being kept as a pet by humans including a dog, a cat, and a rodent. All aspects of the present invention are preferably for the treatment of dogs and/or cats.

The term "dog" includes those dogs which are companion animals such as *Canis familiaris*, working dogs and the like. The term dog is synonymous with the term canine.

The term "cat" includes those cats which are companion animals known as domestic cats or house cats, or *Felis domesticus*. The term cat is synonymous with the term feline.

The phrase "pattern recognition receptor," as used herein is intended to encompass not only Toll Like Receptors and other receptors and receptor classes classified as pattern recognition receptors, but also the proteins of the related signaling pathways that function with and coordinately expressed along with the pattern recognition receptors including, without limitation, MYD88, NOD-1, NOD-2, TIRAP, TIR, TRIF, TRAM, TAK1, TRAF3, TBK1, NEMO, IRAK, IKKi, and TRAF6, and the like as described in, for example, Kawai et al., "The Roles of TLRs, RLRs and NLRs in Pathogen Recognition" *International Immunology* (2009) 21(4): 317-337, and Mahanonda et al., "Toll-Like Receptors and Their Role in Periodontal Health and Disease," *Periodontol* 2000 (2007) 43: 41-55, both of which are hereby incorporated by reference in their entirety.

Methods of the Invention

In one embodiment, the present invention is directed to a method for measuring systemic health in a subject in need thereof, where the subject is afflicted with an oral health condition. This method comprises determining a subject first expression level of a first pattern recognition receptor in the subject and comparing that subject first expression level to a control first expression level of the first pattern recognition receptor. In one aspect of the invention, the healthy control expression level of the first patter recognition receptor is determined in healthy animals that are not afflicted with the oral health condition, i.e., as demonstrated below in the Examples. In another aspect, the healthy control level would be the level of expression in the same animal when the oral cavity is brought to a state of good oral health through intervention (complete dental prophylaxis) or good oral hygiene. Based upon this analysis, it can be concluded that good systemic health in an animal afflicted with an oral health condition is indicated where the value of the first expression level is equal to or less than that of the control. Similarly, were the subject first expression level is greater than that of the healthy control, it can be concluded that the tested animal exhibits poor systemic health, as it relates to the oral health condition.

In another aspect of these embodiments of the invention, the control level of expression of the pattern recognition receptor is the baseline control, measured in the afflicted animal prior to or shortly after treatment of the oral health condition. In this instance increased levels of expression of the pattern recognition receptor (i.e., greater than the baseline control value) is diagnostic of the existence or development of a systemic health condition, while decreased levels of expression of the pattern recognition receptor (i.e., less than the baseline control value) is diagnostic of the amelioration of a systemic health condition in the animal afflicted with an oral health condition.

In certain aspects of these embodiments, the expression level of the pattern recognition receptor can be measured for a pattern recognition receptor selected from the group consisting of Toll Like Receptor 1 (TLR1), Toll Like Receptor 3 (TLR3), Toll Like Receptor 4 (TLR4), Toll Like Receptor 7 (TLR7), Toll Like Receptor 9 (TLR9), Toll Like Receptor 10 (TLR10), myeloid differentiation primary response gene 88 (MYD88), and Nucleotide Binding oligomerization domain containing protein 1 (NOD1).

Another aspect of this embodiment comprises determination of the expression level of at least one second pattern recognition receptor in the subject comparing the subject second expression level to a control second expression level of the second pattern recognition receptor. Again, in one aspect, the control expression levels can be determined in healthy animals not afflicted with the oral health condition. Here, good systemic health in the animal afflicted with the oral health condition is indicated where the value of the second expression level is equal to or less than that of the control, while poor systemic health is indicated in the animal afflicted with the oral health condition where the value of the second expression level is greater than that of the control. The second expression level of the pattern recognition receptor can be measured for a pattern recognition receptor selected from, but not limited to, the group consisting of TLR1, TLR3, TLR4, TLR7, TLR9, TLR10, MYD88, and NOD1. In still another aspect the control level of expression of the second pattern recognition receptor is the baseline control, measured in the afflicted animal prior to or shortly after treatment of the oral health condition. In this instance increased levels of expression of the pattern recognition receptor (i.e., greater than the baseline control value) is diagnostic of the existence, development, and/or progression of a systemic health condition, while decreased levels of expression of the second pattern recognition receptor (i.e., lower than the baseline control value) is diagnostic of the amelioration of a systemic health condition in the animal afflicted with an oral health condition.

In the method described herein the subject or animal tested may be a companion animal. In particular aspects of these embodiments, the companion animal is a feline, while in other aspects, the companion animal is a canine.

In certain embodiments of the methods described herein, expression levels of the pattern recognition receptors are determined by measuring the levels of mRNA encoding the pattern recognition receptor of interest. In one aspect of this embodiment, the mRNA is first converted to cDNA and then measured by quantitative, real time polymerase chain reactions (qRT-PCR), as described in more detail in the Examples. In certain aspects of the present invention, the qRT-PCR data are "normalized" against a "calibrator mRNA."

In one embodiment, the animal to be treated is afflicted with an oral care condition comprising periodontal disease, which may include, without limitation, one or more of gingivitis, periodontitis, dental plaque, dental tartar, resorptive tooth lesion, mobile tooth, attachment loss, and gingival recession.

In another embodiment, the present invention is directed to a method for monitoring the efficacy of a treatment on the systemic health of an animal in need thereof, wherein the animal is afflicted with an oral health condition and wherein the treatment comprises therapy of the oral health condition. This method comprises determining a first expression level of a first pattern recognition receptor in the animal at a first time point, wherein the first time point prior to or shortly after the treatment, followed by determining a second expression level of the first pattern recognition receptor in the animal at a second time point subsequent to the first time point. The values determined for expression level of the pattern recognition receptor are compared and efficacy of the treatment is indicated where first expression level is greater than the second expression level. Again, these expression levels can be determined for one or more than one of a pattern recognition receptor selected from but not limited to the group consisting of TLR1, TLR3, TLR4, TLR7, TLR9, TLR10, MYD88, and NOD1.

In certain embodiments, this method for monitoring efficacy of a treatment may be used where the subject or animal tested is be a companion animal. In particular aspects of these embodiments, the companion animal is a feline, while in other aspects, the companion animal is a canine. In other aspects of this embodiment, the expression levels of the pattern recognition receptor(s) are determined using quantitative real time, polymerase chain reaction analysis (qRT-PCR) of mRNA.

The present invention, in a further embedment, is also directed to a method of determining efficacy of treatment of an oral health condition in an animal in need thereof. This method comprises determining a first expression level of a first pattern recognition receptor in the animal at a first time point. This step is followed by determining a second expression level of the first pattern recognition receptor in the animal at a second time point subsequent to the first time point. The pattern recognition receptor expression levels determined at the two time points are compared and efficacy of the treatment is indicated by the first expression level being greater than the second expression level.

In a still further embodiment, the present invention is directed to a method for diagnosing a systemic health condition in a subject in need thereof, wherein the subject is afflicted with an oral health condition. This method comprises determining a subject first expression level of a first pattern recognition receptor in the subject, and then comparing that expression level to a control first expression level of the first pattern recognition receptor. Again the control value is determined in healthy control animals not afflicted with the oral health condition. Existence of a systemic health condition is indicated by the subject first expression level being greater than the control first expression level and absence of a systemic health condition is indicated by the subject first expression level being less than or equal to the control first expression level. Moreover, in one aspect of this embodiment, severity of the health condition is indicated by the absolute value of a ratio of the subject first expression level to the control first expression level. In another aspect of this embodiment, the control value can be that determined for the subject animal, per se, at a point in time when the animal was healthy and was not afflicted with either an oral health condition or a systemic health condition.

In certain aspects of these embodiments, the expression levels can be determined for one or more than one of a pattern recognition receptor selected from, but not limited to, the group consisting of TLR1, TLR3, TLR4, TLR7, TLR9, TLR10, MYD88, and NOD1.

In other aspects of this embodiment, the subject is a companion animal, e.g., a feline or a canine.

The oral health condition afflicting the subjects and animals for which the described methods are carried out, comprise at least one of periodontal disease, including, e.g., one or more of gingivitis and periodontitis, dental plaque, dental tartar, gingival recession, gingival attachment loss, and mobile tooth.

The present invention is also directed to a method for treating a chronic systemic inflammation in an animal in need thereof and afflicted with an oral health condition. The method comprises subjecting the animal to a dental prophylaxis treatment designed to ameliorate one or more oral health conditions, which may comprise periodontal disease, which may include gingivitis and periodontitis, dental plaque, dental tartar, gingival recession, gingival attachment loss, mobile tooth, and combinations of two or more thereof.

In certain embodiments, the animal tested or treated according to the methods described herein is an animal afflicted with an oral care condition and in need of such testing. In certain embodiments, that animal is a non-human animal, or a non-human mammal, e.g., a non-human primate (e.g., monkeys, chimpanzees, apes etc.), a companion animal, or a house pet (e.g., dog, cat, rabbit etc.), a laboratory animal, a domesticated animal (including livestock and farm animals such as but not limited to horses, goats, sheep, swine, llamas, alpacas, bovine animals etc.). In one embodiment, the animal is a domesticated companion animal or "house" pet, such as canine or a feline. In one aspect, the animal is a dog. In another aspect the animal is a cat.

Kits of the Invention

The present invention is further directed to kits useful in the practice of the methods described herein, i.e., useful for determining the expression level of one or more feline pattern recognition receptors. In one embodiment, the kit comprises forward and reverse primers suitable for polymerase chain reaction amplification of cDNA corresponding to at least one pattern recognition receptor selected from, but not limited to, the group consisting of feline Toll Like Receptor 1 (TLR1), feline Toll Like Receptor 3 (TLR3), feline Toll Like Receptor 4 (TLR4), feline Toll Like Receptor 7 (TLR7), feline Toll Like Receptor 9 (TLR9), feline Toll Like Receptor 10 (TLR10), feline myeloid differentiation primary response gene 88 (MyD88), and feline Nucleotide Binding oligomerization domain containing protein 1 (NOD1).

In another embodiment, a kit of the invention is useful for determination of the expression level of one or more canine pattern recognition receptors. In one aspect of this embodiment, the kit comprises forward and reverse primers suitable for polymerase chain reaction amplification of cDNA corresponding to at least one pattern recognition receptor selected from the group consisting of, but not limited to, canine Toll Like Receptor 1 (TLR1), canine Toll Like Receptor 3 (TLR3), canine Toll Like Receptor 4 (TLR4), canine Toll Like Receptor 7 (TLR7), canine Toll Like Receptor 9 (TLR9), feline Toll Like Receptor 10 (TLR10), canine myeloid differentiation primary response gene 88 (MyD88), and canine Nucleotide Binding oligomerization domain containing protein 1 (NOD1).

In particular aspects of these embodiments, the kits can contain one or more of primers or pairs of primers useful for PCR analysis, as set forth in the Examples, below, (e.g., SEQ ID NO. 1-SEQ ID NO. 16) or those readily designed, e.g., using commercially-available software based on sequences corresponding to the gene expression level to be analyzed (e.g., SEQ ID NO. 17-SEQ ID NO. 31).

EXAMPLES

The studies described herein were conducted with cats and document the effect of periodontal disease on systemic pattern recognition receptor expression, demonstrating a causal connection between oral and systemic health. In the pilot study describe below, pattern recognition receptors (TLR1, TLR3, TLR4, TLR7, TLR9, TLR10, MYD88, and NOD1) were shown to be differentially expressed in cats with good oral health as compared to cats with poor oral health. In a first intervention study, it was shown that cats with poor oral health have up-regulated systemic pattern recognition receptor expression levels compared to those same cats with healthy mouths, and that a complete dental prophylaxis attenuates systemic expression of these mediators of host immune response. These results were reproduced in a second intervention study in which the cats with severe periodontal disease were brought to a state of good oral health with a concomitant, statistically significant, reduction in the systemic expression levels of three pattern recognition receptors. In addition, it was noted that there was a clear numerical decrease in expression levels of all the pattern recognition receptor levels as a function of oral health intervention that was seen for only one pattern recognition receptor (TLR10) in control animals. Taken together, the data presented herein provide strong evidence supporting systemic response to poor oral health, thereby establishing a causal connection between oral and systemic health.

Published reviews describing the roles played by pattern recognition receptors, the related signaling pathways and proteins thereof, and biochemical consequences of pattern receptor recognition ligand binding are provided, inter alia, in Kawai et al., "The Roles of TLRs, RLRs and NLRs in Pathogen Recognition" *International Immunology* (2009) 21(4): 317-337 and Mahanonda et al., "Toll-Like Receptors and Their Role in Periodontal Health and Disease," *Periodontol* 2000 (2007) 43: 41-55, both of which are hereby incorporated by reference in their entirety.

Materials and Methods

Sample Collection: Samples of feline whole blood were collected into PAXgene blood RNA tubes (Qiagen, Valencia, Calif.) and frozen until analysis. These blood samples were used to assess expression levels of the pattern recognition receptors (TLR1, TLR3, TLR4, TLR7, TLR9, TLR10, MYD88, and NOD1).

cDNA Synthesis: cDNA was prepared from the collected mRNA using the Ovation™ System (NuGen Technologies, San Carlos, CAP) according to the manufacturer's instructions.

Primers, Annealing Temperatures, and Thermal Cycler Programming: For primer annealing and first strand synthesis, the following program was used: samples were maintained at 65° C. for 5 minutes followed by a return to 4° C. and holding at that temperature until subsequent steps were to be performed. Amplification primers used included those of SEQ ID NO:1 (forward primer for analysis of feline TLR 9); SEQ ID NO:2 (reverse primer for analysis of feline TLR 9); SEQ ID NO:3 (forward primer for analysis of feline TLR 10); SEQ ID NO:4 (reverse primer for analysis of feline TLR 10); SEQ ID NO:5 (forward primer for analysis of feline NOD1); SEQ ID NO:6 (reverse primer for analysis of feline NOD1); SEQ ID NO:7 (forward primer for analysis of feline MYD88); SEQ ID NO:8 (reverse primer for analysis of feline MYD88); SEQ ID NO:9 (forward primer for analysis of feline TLR 1); SEQ ID NO:10 (reverse primer for analysis of feline TLR 1); SEQ ID NO:11 (forward primer for analysis of feline TLR 3); SEQ ID NO:12 (reverse primer for analysis of feline TLR 3); SEQ ID NO:13 (forward primer for analysis of feline TLR 4); SEQ ID NO:14 (reverse primer for analysis of feline TLR 4); SEQ ID NO:15 (forward primer for analysis of feline TLR 7); and SEQ ID NO:16 (reverse primer for analysis of feline TLR 7).

The relevant nucleotide sequences for feline TLR 9, TLR 10, NOD1, MYD88, TLR1, TLR3, TLR 4 and TLR 7 are provided in SEQ ID NO:17 to SEQ ID NO: 24, respectively. The relevant nucleotide sequences for canine TLR9, TLR2, TLR4, TLR7, CAM1, TLR1, and MYD88 are provided in SEQ ID NO: 25 TO SEQ ID NO: 31, respectively.

After annealing, first strand synthesis was carried out by incubation at 48° C. for 60 minutes, incubation at 70° C. for 15 minutes, followed by a return to 4° C. and holding at that temperature until subsequent steps were to be performed.

Second strand synthesis was carried out, incubating the samples at 37° C. for 30 minutes, and then 75° C. for 15 minutes, followed by a return to 4° C. and holding at that temperature until subsequent steps were to be performed.

SPIA® Amplification (NuGEN Technologies, San Carlos, Calif.): Amplification was carried out at 48° C. for 30 minutes, followed by a hold at 4° C., and then at 48° C. for 30 minutes, and 95° C. for 5 minutes, followed by a hold at 4° C.

Quantitative, real time polymerase chain reaction (qRT-PCR), was carried out using an Applied Biosystems (Torrance Calif.) 7500 Fast Real-Time PCR System and 7500 Software 2.0.1.

Gene Expression Calculations: The Comparative Ct method (ΔΔCt-method): The comparative Ct method is a mathematical model that calculates changes in expression of the gene of interest after the dental treatment, relative to that of a calibrator. Prior to experimental sample analysis, a validation experiment was run to ensure that the amplification efficiencies of the gene of interest and the reference gene or "housekeeping" gene are equal. The validation experiment consisted of a dilution series of cDNA containing the genes of interest (pattern recognition receptors) and the reference gene (18S). The slopes of a semi-log regression analysis of the dilution series (ΔCt vs. log input amount) should be approximately equal for a valid ΔΔCT calculation (±0.1). Assessing the relative efficiencies of the target gene of interest amplification and the reference endogenous control amplification was achieved by running serial dilutions using one pooled sample. The CT values generated from each dilution point (target vs. reference) were used in the ΔCT calculation (ΔCT=CT target−CT reference). All of the genes of interest passed this validation test.

Statistical Analysis and Methods: Fold Change. Data Assist™ v. 3.0 Software (Applied Biosystems) was used for data analysis which uses the comparative CT method for calculating relative quantification of gene expression. It contains a filtering procedure for removal of outliers, various normalization methods based on single or multiple genes, and provides relative quantification analysis of gene expression through a combination of statistical analysis and interactive visualization. A p-value cut off of 0.05 was used to select significant gene expression differences from the results obtained from the DataAssist software.

Example 1: Pilot Study

This experiment was intended to determine whether or not pattern recognition receptors (TLR1, TLR3, TLR4, TLR7, TLR9, TLR10, MYD88, and NOD1) were differentially expressed in cats with good oral health as compared to cats with poor oral health.

In this study age matched cats were selected from among those undergoing their annual dental prophylaxis and that were deemed to be in either good or poor oral health at the time of this procedure. Selection was done by examination of their oral health status that was recorded just prior to their dental cleaning. Particular attention was paid to gingivitis status because a systemic response to poor oral health was hypothesized to be influenced by this metric. Two groups of cats were established, each with seventeen members; one with "poor" oral health and the other with relatively good oral health.

With respect to the "poor" oral health group, (1) all seventeen members were deemed to have "severe" gingivitis; (2) plaque was characterized as "medium" in sixteen members and "heavy" in one member, and (3) calculus was characterized as "light" in two members, "medium" in ten members, and "heavy" in five members.

With respect to the "good" oral health group, (1) all seventeen members were deemed to have "mild" gingivitis; (2) plaque was characterized as "light" in all seventeen members, and (3) calculus was characterized as "light" in fourteen members, and "medium" in three members.

Blood samples from these cats were collected into PAXgene blood RNA tubes and stored frozen until analysis. mRNA was isolated from these samples and RNA encoding the Pattern Recognition Receptor (PRR) mRNA for TLR1, TLR3, TLR4, TLR7, TLR9, TLR10, MYD88, and NOD1, was converted to double-stranded DNA and amplified by qRT-PCR, according to the methods described above.

Quantitative analysis of these blood samples showed that, numerically, all of the pattern recognition receptors were up-regulated in cats with periodontal disease, even though only the TLR10 expression differences were statistically different. NOD1 and TLR7 showed an elevated expression level in cats with periodontal disease relative to the set of cats with "good" oral health, with these differences trending toward statistical significance ($0.05 < p < 0.10$), as demonstrated in Table 1, below.

TABLE 1

| PRR Target | AVG Δ Ct Poor Oral Health Set | AVG Δ Ct Good Oral Health Set | ΔΔ Ct: Good/Poor Oral Health | Fold Change | P-Value |
| --- | --- | --- | --- | --- | --- |
| MYD88 | −2.81 | −2.44 | −0.37 | 1.29 | 0.55 |
| NOD1 | 4.38 | 5.58 | −1.19 | 2.29 | 0.06 |
| TLR1 | −6.96 | −6.11 | −0.85 | 1.80 | 0.13 |
| TLR10 | −1.20 | 0.43 | −1.62 | 3.08 | 0.03 |
| TLR 3 | 3.34 | 4.55 | −1.22 | 2.32 | 0.17 |
| TLR4 | −1.55 | −1.12 | −0.44 | 1.35 | 0.52 |
| TLR7 | 1.35 | 2.27 | −0.92 | 1.90 | 0.06 |
| TLR9 | 0.47 | 1.28 | −0.82 | 1.76 | 0.23 |

The data of Table 1 illuminate the pilot study differential pattern recognition receptor expression between the cats of the "poor" oral health group and that of the "good" oral health group of cats. The Fold Change is the difference between the cats of the "poor" oral health group and that of the "good" oral health group of cats. Statistically significant differences are identified as those with a P-value less than 0.05 and those data indicating a trend toward significance are those with a P-value greater than 0.05 but less than 0.1.

As demonstrated by the above data this study demonstrated that pattern recognition receptors (TLR1, TLR3, TLR4, TLR7, TLR9, TLR10, MYD88, and NOD1) were differentially expressed in cats with good oral health as compared to cats with poor oral health.

Example 2: First Intervention Study

This first intervention study was designed to determine whether or not the expression levels of the pattern recognition receptors (TLR1, TLR3, TLR4, TLR7, TLR9, TLR10, MYD88, and NOD1) would respond to oral care therapy, e.g., periodontal disease intervention, and thereby establish a causal link between oral health and systemic health.

Thirteen cats were selected from a laboratory feline colony that could be classified as having "poor" oral health, as determined by a gingivitis score classified as "severe" upon initial visual inspection. Prior to initiation of the study, multiple measures of oral health were documented for each cat. These measures included dental plaque, tartar, toot stain, and gingivitis using metrics from the Logan/Boyce dental substrate quantification method (Logan et al. (1994) "Oral health assessment in dogs: parameters and methods" *J. Vet. Dent.* 11(2): 58-63), as well as the number of missing teeth, the number of mobile teeth, the number of teeth with gingival recession, the sum of the recession scores, the average recession score, the number of teeth with pockets greater than 1 mm, the average pocket depth greater than 1 mm, the number of teeth with furcations, the average furcation grade, the number of teeth with resorptive lesions, and then number of teeth with fractures.

The average gingivitis score for the group was 1.0±0.2 with values ranging from 0.6 to 1.3. Since the range of possible scores for gingivitis according to the method used is between 0.3 and 3, the average of 1.0 would be considered to be moderate inflammation. In contrast, plaque and calculus scores were high, with averages of 12.6 and 5.0, respectively. Possible plaque scores range from 0 to 24 and possible calculus scores range from 0 to 12 so the cats with the values stated were considered to have substantial substrate accumulation. The scoring standards for grading gingivitis, dental plaque, and calculus, are provided in Tables 2, 3, and 4, respectively.

Table 2 provides the criteria for grading gingivitis. Scored gingivae are divided vertically into mesial, buccal, and distal thirds, and each third receives a separate numerical score based on the degree of gingival inflammation using the scale below. For each tooth, the scores for each third are averaged to obtain a whole-tooth score, and the sum of the whole-tooth scores divided by the number of teeth scored is the final, whole-mouth gingival score.

TABLE 2

| Gingivitis Scoring | |
|---|---|
| 0 | Normal Gingiva |
| 0.5 | Normal inflammation; slight redness |
| 1.0 | Moderate inflammation and redness; no bleeding on probing |
| 2.0 | Moderate inflammation with sever redness; bleeding on probing |
| 3.0 | Severe inflammation and redness, edema, ulceration, and spontaneous bleeding |

Table 3 provides the grading criteria for dental plaque. Plaque is disclosed with a 2% eosin solution. The facial surface of each elevated tooth is divided horizontally, and each half is assigned a separate numerical score based on percent plaque coverage and dye intensity found in the Table 3 below. For each half, coverage is multiplied by intensity, and the results are summed to obtain a whole-tooth plaque score. The sum of the whole-tooth plaque scores is divided by the number of teeth scored to obtain a whole-mouth plaque score.

TABLE 3

| Percent Coverage | | Intensity | |
|---|---|---|---|
| 0 | No plaque detected | | |
| 1 | Plaque coverage <25% | 1 | Light (pink) |
| 2 | Plaque coverage 25 to <50% | 2 | Medium (red) |

TABLE 3-continued

| Percent Coverage | | Intensity | |
|---|---|---|---|
| 3 | Plaque coverage 50 to <75% | 3 | Dark (deep red) |
| 4 | Plaque coverage 75 to <100% | | |

Table 4 provides the criteria for grading calculus. The facial surface of each evaluated tooth is divided into vertical thirds, and each third is assigned a separate numerical score based on the percent coverage using the scale set forth in Table 4 below. Coverage scores for each tooth are added to obtain a whole-tooth calculus score, and the sum of the whole-tooth calculus scores divided by the number of teeth scored is the final whole-mouth calculus score.

TABLE 4

| Percent Coverage | |
|---|---|
| 0 | No calculus detected |
| 1 | Calculus coverage <25% |
| 2 | Calculus coverage 25 to <50% |
| 3 | Calculus coverage 50 to <75% |
| 4 | Calculus coverage 75 to <100% |

Fasting blood samples were drawn just prior to and just after a complete dental prophylaxis performed according to standard procedure on day 1. Additional blood samples were taken on day 3, 8, and 15 after the complete dental prophylaxis. All blood samples were collected into PAXgene blood RNA tubes using standard procedures, and the samples were frozen until analysis. These blood samples were used to assess the expression levels of the PRRs (TLR1, TLR3, TLR4, TLR7, TLR9, TLR10, MYD88, and NOD1) by qRT-PCR, according to the method described above.

Quantification of the relative levels of expression of the pattern recognition receptors targeted in this study is presented in Table 5.

TABLE 5

| Target | Day | Median ΔCt | Median ΔΔCt | Median RQ | Median Fold Change | P-value | Mean ΔCt | Mean ΔΔCt | Mean RQ | Mean Fold Change |
|---|---|---|---|---|---|---|---|---|---|---|
| MYD88 | Pre | 13.80 | 0.00 | 1.000 | 1.000 | — | 14.08 | 0.00 | 1.00 | 1.00 |
| MYD88 | Post | 13.75 | −0.04 | 1.026 | 1.026 | 0.6419 | 13.74 | −0.34 | 1.27 | 1.27 |
| MYD88 | 3 | 12.68 | −1.12 | 2.172 | 2.172 | 0.1290 | 11.35 | −2.73 | 6.64 | 6.64 |
| MYD88 | 8 | 13.44 | −0.36 | 1.284 | 1.284 | 0.5695 | 13.67 | −0.41 | 1.33 | 1.33 |
| MYD88 | 15 | 15.67 | 1.87 | 0.274 | −3.655 | 0.1615 | 15.29 | 1.21 | 0.43 | −2.31 |
| NOD1 | Pre | 15.90 | 0.00 | 1.000 | 1.000 | − | 16.70 | 0.00 | 1.00 | 1.00 |
| NOD1 | Post | 16.07 | 0.17 | 0.886 | −1.128 | 0.4951 | 16.02 | −0.68 | 1.60 | 1.60 |
| NOD1 | 3 | 16.13 | 0.23 | 0.852 | −1.174 | 0.3222 | 14.87 | −1.83 | 3.56 | 3.56 |
| NOD1 | 8 | 16.96 | 1.06 | 0.480 | −2.082 | 0.9179 | 16.81 | 0.11 | 0.93 | −1.08 |
| NOD1 | 15 | 18.95 | 3.06 | 0.120 | −8.316 | 0.0429 | 18.83 | 2.12 | 0.23 | −4.36 |
| TLR1 | Pre | 6.54 | 0.00 | 1.000 | 1.000 | — | 6.60 | 0.00 | 1.00 | 1.00 |
| TLR1 | Post | 6.47 | −0.07 | 1.049 | 1.049 | 0.7705 | 6.38 | −0.22 | 1.16 | 1.16 |
| TLR1 | 3 | 6.46 | −0.08 | 1.057 | 1.057 | 0.4802 | 5.39 | −1.22 | 2.32 | 2.32 |
| TLR1 | 8 | 7.45 | 0.92 | 0.530 | −1.887 | 0.2237 | 7.52 | 0.91 | 0.53 | −1.89 |
| TLR1 | 15 | 8.98 | 2.45 | 0.183 | −5.459 | 0.0019 | 9.28 | 2.68 | 0.16 | −6.40 |
| TLR10 | Pre | 15.26 | 0.00 | 1.000 | 1.000 | — | 14.75 | 0.00 | 1.00 | 1.00 |
| TLR10 | Post | 13.50 | −1.76 | 3.380 | 3.380 | 0.1846 | 13.75 | −1.00 | 1.99 | 1.99 |
| TLR10 | 3 | 15.43 | 0.17 | 0.887 | −1.128 | 0.7306 | 14.10 | −0.65 | 1.56 | 1.56 |
| TLR10 | 8 | 14.67 | −0.59 | 1.506 | 1.506 | 0.4993 | 15.29 | 0.54 | 0.69 | −1.45 |
| TLR10 | 15 | 16.24 | 0.98 | 0.507 | −1.973 | 0.0202 | 16.83 | 2.08 | 0.24 | −4.22 |
| TLR4 | Pre | 13.50 | 0.00 | 1.000 | 1.000 | — | 13.56 | 0.00 | 1.00 | 1.00 |
| TLR4 | Post | 13.40 | −0.10 | 1.071 | 1.071 | 0.7047 | 13.27 | −0.29 | 1.23 | 1.23 |
| TLR4 | 3 | 12.48 | −1.02 | 2.021 | 2.021 | 0.1861 | 10.84 | −2.72 | 6.61 | 6.61 |
| TLR4 | 8 | 12.87 | −0.63 | 1.551 | 1.551 | 0.8882 | 13.46 | −0.10 | 1.07 | 1.07 |
| TLR4 | 15 | 14.93 | 1.43 | 0.370 | −2.700 | 0.0452 | 15.21 | 1.65 | 0.32 | −3.13 |
| TLR7 | Pre | 14.60 | 0.00 | 1.000 | 1.000 | — | 14.89 | 0.00 | 1.00 | 1.00 |
| TLR7 | Post | 15.34 | 0.74 | 0.597 | −1.676 | 0.5124 | 15.54 | 0.64 | 0.64 | −1.56 |
| TLR7 | 3 | 14.61 | 0.02 | 0.989 | −1.011 | 0.5166 | 13.71 | −1.18 | 2.27 | 2.27 |
| TLR7 | 8 | 15.91 | 1.31 | 0.402 | −2.847 | 0.1782 | 16.17 | 1.28 | 0.41 | −2.43 |
| TLR7 | 15 | 17.04 | 2.45 | 0.183 | −5.542 | 0.0018 | 17.91 | 3.02 | 0.12 | −8.11 |

TABLE 5-continued

| Target | Day | Median ΔCt | Median ΔΔCt | Median RQ | Median Fold Change | P-value | Mean ΔCt | Mean ΔΔCt | Mean RQ | Mean Fold Change |
|---|---|---|---|---|---|---|---|---|---|---|
| TLR9 | Pre | 14.57 | 0.00 | 1.000 | 1.000 | — | 14.93 | 0.00 | 1.00 | 1.00 |
| TLR9 | Post | 14.76 | 0.19 | 0.879 | −1.137 | 0.9416 | 14.88 | −0.06 | 1.04 | 1.04 |
| TLR9 | 3 | 14.89 | 0.32 | 0.801 | −1.248 | 0.3711 | 13.39 | −1.55 | 2.92 | 2.92 |
| TLR9 | 8 | 16.55 | 1.97 | 0.255 | −3.925 | 0.3668 | 15.71 | 0.78 | 0.58 | −1.72 |
| TLR9 | 15 | 17.20 | 2.63 | 0.162 | −6.175 | 0.0237 | 17.20 | 2.27 | 0.21 | −4.82 |

The P-value of Table 5 is the median, comparing the value at each time point with the "pre-prophylaxis treatment" sample. Similarly, the Fold Change is the derived as the median ΔCt or as the mean ΔCt. The "pre" and "post" entries refer to the Day 1 blood samples taken, respectively, before and after the dental prophylaxis.

Prior to dental intervention, these expression levels were higher than they were after the cats' oral health improved. The data suggest that there were no immediate responses to prophylaxis; i.e., there was very little change from the pre- to post-prophylaxis time points, but the expression levels of each of the pattern recognition receptors dropped to below baseline (pre-prophylaxis) levels by the end of the study. Only MYD88 did not show a significant, or near significant reduction fourteen days after treatment.

In this study, the expression of TLR1, TLR4, TLR7, TLR9, TLR10, and NOD1 showed a significant response to periodontal disease intervention on day 15, i.e., 14 days after the dental prophylaxis. MYD88 showed a numerical response that paralleled the others, but was not statistically significant. After day 3, the expression levels of all of the pattern recognition receptors dropped, ultimately to levels lower than they were at base line. These data further indicate that pattern recognition receptors are useful as systemic markers of periodontal disease, status, for example but not limited to, bacteremia associated with periodontal disease or arising from "leakage" of oral pathogens into the body during, e.g., professional dental cleaning.

The data provided above, demonstrating that expression levels of pattern recognition receptors (TLR1, TLR3, TLR4, TLR7, TLR9, TLR10, MYD88, and NOD1) responded to oral care therapy, e.g., periodontal disease intervention, establish that there is in fact a causal link between oral health and systemic health.

Example 2: Second Intervention Study

This second intervention study was also designed to determine whether or not the expression levels of the pattern recognition receptors (TLR1, TLR3, TLR4, TLR7, TLR9, TLR10, MYD88, and NOD1) would respond to oral care therapy, e.g., periodontal disease intervention, and thereby establish a causal link between oral health and systemic health.

A total of 48 cats with severe periodontal disease where randomized into two groups, with Group I containing 30 cats and Group II containing 18 cats. Pre-existing dental disease was evaluated using a semi-quantitative visual scoring system graded on a scale of from 0 to 4. The two groups were compared prior to treatment to ensure that there was no significant difference in apparent severity. Cats were maintained on their staple canned diet throughout the experimental period in controlled conditions.

Initially, blood samples were taken from all cats to assess pattern recognition receptor expression prior to intervention, i.e., at Day −16. Sixteen days after this initial blood collection, periodontal disease treatments were performed on the 30 cats of the Test Group (Group I). Treatment of the periodontal disease of the control cats was performed later in the study and their pattern recognition receptor expression levels provided reference ("untreated") values. All cats received amoxicillin/clavulanate immediately pre-op but nothing post-op (except for 1 cat, which required additional treatment with buprenorphine and amoxicillin/clavulanate, before being returned to the study).

All cats received buprenorphine (40 μg/kg s/c) immediately pre-op, which was carried out under standard conditions. None of the cats were administered non-steroidal anti-inflammatory drugs at any point during this study.

Blood samples were also collected 16, 45, 90, and 180 days after treatment in the Test Group (Group I) and 16, 45, and 90 days after treatment in the Control Group (Group II). All blood samples were collected into PAXgene blood RNA tubes under standard conditions and stored frozen until analysis. These blood samples were used to assess the expression levels of TLR1, TLR4, TLR7, TLR9, TLR10, MYD88, and NOD1 by qRT-PCR, according to the methods described above.

The PCR analysis was carried out twice. In the initial analysis, pattern recognition receptor expression levels for all the available RNA samples for both the Test and Control groups were assessed and the results blended at baseline. However, in this initial study, only the available Test Group RNA samples were assessed at the additional time points. The second analysis was run and focused specifically on the Day −16 and Day +16 time points. Again the pattern recognition receptor expression levels for the available RNA samples from both the Test and Control Groups were assessed and the results blended at baseline. However, the Day +16 Test and Control Group pattern recognition receptor expression levels were kept separate, with the expectation that this method of analysis would differentiate between pattern recognition receptor expression levels that changed as a function of treatment (i.e., Test Group cats), and would also identify any changes that may have occurred as a function of time rather than treatment (i.e., Control Group cats). In addition, the second analysis used a different "housekeeping" gene than in the first analysis to reduce the variability of the assay.

Gingivitis scores for the two groups (Test and Control) of cats averaged 2.2 of a possible 4, indicating significant gingivitis. Initial analysis of pattern recognition receptor expression levels from all of the cats as baseline, but only the Test Group of cats post-prophylaxis showed a significant decrease as a function of treatment in all but TLR7. In all cases there was a numerical decrease in pattern recognition receptor expression levels at the first data point post-pro- phylaxis (Day +16). However, after the Day 45 time point, all pattern recognition receptor expression levels returned to lower levels, ending at levels significantly below the baseline values at Day 180, as indicated in Table 6, below.

TABLE 6

| Target | Day | Average ΔCt | Median ΔCt | ΔΔCt | RQ | Fold Change | P-value |
|---|---|---|---|---|---|---|---|
| MYD88 | −16 | 5.1 | 4.9 | 0.00 | 1.00 | 1.00 | — |
| MYD88 | 16 | 6.9 | 7.4 | 2.5 | 0.2 | −5.8 | 0.0497 |
| MYD88 | 45 | 4.8 | 4.3 | −0.5 | 1.4 | 1.4 | 0.7283 |
| MYD88 | 90 | 5.1 | 5.6 | 0.7 | 0.6 | −1.7 | 0.9559 |
| MYD88 | 180 | 7.4 | 7.5 | 2.7 | 0.2 | −6.3 | 0.0033 |
| NOD1 | −16 | 9.4 | 9.3 | 0.00 | 1.00 | 1.00 | — |
| NOD1 | 16 | 11.7 | 11.8 | 2.5 | 0.2 | −5.6 | 0.0156 |
| NOD1 | 45 | 9.4 | 9.4 | 0.1 | 1.0 | −1.0 | 0.9677 |
| NOD1 | 90 | 9.6 | 9.8 | 0.4 | 0.8 | −1.3 | 0.8297 |
| NOD1 | 180 | 12.3 | 12.0 | 2.6 | 0.2 | −6.1 | 0.0004 |
| TLR1 | −16 | 2.3 | 2.4 | 0.00 | 1.00 | 1.00 | — |
| TLR1 | 16 | 4.2 | 4.9 | 2.5 | 0.2 | −5.5 | 0.0353 |
| TLR1 | 45 | 3.0 | 2.9 | 0.4 | 0.7 | −1.3 | 0.3939 |
| TLR1 | 90 | 3.1 | 3.3 | 0.9 | 0.5 | −1.8 | 0.3582 |
| TLR1 | 180 | 5.1 | 4.5 | 2.1 | 0.2 | −4.2 | 0.0036 |
| TLR10 | −16 | 7.8 | 7.2 | 0.00 | 1.00 | 1.00 | — |
| TLR10 | 16 | 9.1 | 9.7 | 2.5 | 0.2 | −5.6 | 0.1510 |
| TLR10 | 45 | 7.9 | 8.4 | 1.2 | 0.4 | −2.4 | 0.8763 |
| TLR10 | 90 | 8.3 | 8.9 | 1.7 | 0.3 | −3.3 | 0.5327 |
| TLR10 | 180 | 9.6 | 9.0 | 1.8 | 0.3 | −3.6 | 0.112 |
| TLR4 | −16 | 5.3 | 5.6 | 0.00 | 1.00 | 1.00 | — |
| TLR4 | 16 | 8.1 | 8.7 | 3.2 | 0.1 | −8.9 | 0.0044 |
| TLR4 | 45 | 5.1 | 5.4 | −0.1 | 1.1 | 1.5 | 0.9087 |
| TLR4 | 90 | 5.4 | 6.0 | 0.4 | 0.8 | −1.3 | 0.8397 |
| TLR4 | 180 | 7.4 | 7.6 | 2.0 | 0.3 | −4.0 | 0.0160 |
| TLR7 | −16 | 8.8 | 9.0 | 0.00 | 1.00 | 1.00 | — |
| TLR7 | 16 | 10.2 | 10.9 | 1.9 | 0.3 | −3.6 | 0.1593 |
| TLR7 | 45 | 8.6 | 8.9 | −0.2 | 1.1 | 1.1 | 0.8069 |
| TLR7 | 90 | 8.9 | 9.0 | 0.0 | 1.0 | 1.0 | 0.8478 |
| TLR7 | 180 | 10.1 | 10.6 | 1.6 | 0.3 | −3.0 | 0.1030 |
| TLR9 | −16 | 8.6 | 8.4 | 0.00 | 1.00 | 1.00 | — |
| TLR9 | 16 | 10.7 | 11.3 | 2.9 | 0.1 | −7.5 | 0.0396 |
| TLR9 | 45 | 8.5 | 8.1 | −0.3 | 1.3 | 1.5 | 0.9717 |
| TLR9 | 90 | 8.9 | 8.7 | 0.2 | 0.9 | −1.2 | 0.7011 |
| TLR9 | 180 | 11.2 | 11.4 | 2.9 | 0.1 | −7.6 | 0.0018 |

Focusing on the on the early time points, it is apparent that there was a clear and significant decrease in most systemic pattern recognition receptor expression levels as a function of oral health intervention. This result is comparable to that obtained in the first intervention study described above.

Comparing only the pre- and post-prophylaxis time points, i.e., Day −16 and Day +16, for both the Test and Control Groups of cats in a reanalysis of this experiment using a different gene as reference provided results similar to those of the initial analysis described above. The expression levels of all of the pattern recognition receptors were numerically reduced from baseline for the Test Group cats, but were unchanged for the Control Group cats (with the exception of TLR 10). The changes for the Test Group cats were statistically significant for TLR1 and TLR7. TLR10 expression levels were down-regulated for both the Test Group cats and the Control Group cats, indicating an effect of time but not of treatment for expression of this pattern recognition receptor.

The data provided above in Example 3, again demonstrate that expression levels of pattern recognition receptors (TLR1, TLR3, TLR4, TLR7, TLR9, TLR10, MYD88, and NOD1) respond to oral care therapy, e.g., periodontal disease intervention, further reinforcing the existence of a causal link between oral health and systemic health.

The collected data obtained and set forth above demonstrate that (a) some pattern recognition receptor expression levels in cats with periodontal disease are significantly higher than in those same cats with good oral health, (b) communication exists between the oral cavity and the rest of the body, as evidenced by the up-regulation of pattern recognition receptor expression in cats with periodontal disease, and (c) oral health intervention in the form of a complete dental prophylaxis attenuates a systemic consequence of oral disease. Because leakage of bacteria from the oral cavity into the rest of the body may be regular or continuous in diseased animals, it is likely to result in the regular or continuous up-regulation of pattern regulation receptor expression. This in turn may initiate a more comprehensive immune response, contributing to a chronic systemic inflammatory burden.

What is claimed is:

1. A method for monitoring efficacy of a treatment on the systemic health of an animal in need thereof, the method comprising:
- determining a first expression level of a first pattern recognition receptor in the animal at a first time point, wherein the first time point is prior to treatment;
- determining a second expression level of the first pattern recognition receptor in the animal at a second time point subsequent to the first time point and after treatment; and
- comparing the first expression level to the second expression level;
wherein efficacy of the treatment is indicated by the first expression level being greater than the second expression level;
- wherein the animal is afflicted with an oral health condition, and
- wherein the treatment comprises therapy of the oral health condition.

2. The method of claim 1, wherein the first pattern recognition receptor comprises one or more of Toll Like Receptor 1 (TLR1), Toll Like Receptor 3 (TLR3), Toll Like Receptor 7 (TLR7), Toll Like Receptor 9 (TLR9), Toll Like Receptor 10 (TLR10), myeloid differentiation primary response gene 88 (MyD88), Nucleotide Binding oligomerization domain containing protein 1 (NOD1), or combinations thereof.

3. The method of claim 1, wherein the first pattern recognition receptor is selected from the group consisting of Toll Like Receptor 1 (TLR1), Toll Like Receptor 3 (TLR3), Toll Like Receptor 7 (TLR7), Toll Like Receptor 9 (TLR9), Toll Like Receptor 10 (TLR10), myeloid differentiation primary response gene 88 (MyD88), Nucleotide Binding oligomerization domain containing protein 1 (NOD1), and combinations thereof.

4. The method of claim 1, further comprising measuring a decrease of at least a two-fold change in the expression of the first expression level relative to the second expression level, wherein the decrease of at least a two-fold change in the expression level of the first expression level relative to the second expression level indicates the animal having poor systemic health.

5. The method of claim 1, further comprising treating the animal by subjecting the animal to a treatment designed to ameliorate the oral health condition, wherein treating the animal decreases expression of the first pattern recognition receptor.

6. The method of claim 1, wherein the animal is a companion animal.

7. The method of claim 6, wherein the companion animal is a feline.

8. The method of claim 6, wherein the companion animal is a canine.

9. The method of claim 1, wherein the first expression level and the second expression level are determined by measuring the levels of mRNA encoding the respective pattern recognition receptors.

10. The method of claim 9, wherein calculation of the first expression level and the second expression level comprises normalization of data relative to that of a calibrator mRNA.

11. The method of claim 1, wherein the oral health condition comprises at least one of gingivitis, periodontitis, dental plaque, dental tartar, pocket depth, mobile tooth, attachment loss, gingival recession, or combinations thereof.

12. A method of determining efficacy of treatment of an oral health condition in an animal in need thereof, the method comprising:
- determining a first expression level of a first pattern recognition receptor in the animal at a first time point, wherein the first time point is prior to the treatment;
- determining a second expression level of the first pattern recognition receptor in the animal at a second time point subsequent to the first time point and after treatment; and
- comparing the first expression level to the second expression level; and
- wherein efficacy of the treatment is indicated by the first expression level being greater than the second expression level.

13. The method of claim 12, wherein the first pattern recognition receptor comprises one or more of Toll Like Receptor 1 (TLR1), Toll Like Receptor 3 (TLR3), Toll Like Receptor 7 (TLR7), Toll Like Receptor 9 (TLR9), Toll Like Receptor 10 (TLR10), myeloid differentiation primary response gene 88 (MyD88), Nucleotide Binding oligomerization domain containing protein 1 (NOD1), or combinations thereof.

14. The method of claim 12, wherein the first pattern recognition receptor is selected from the group consisting of Toll Like Receptor 1 (TLR1), Toll Like Receptor 3 (TLR3), Toll Like Receptor 7 (TLR7), Toll Like Receptor 9 (TLR9), Toll Like Receptor 10 (TLR10), myeloid differentiation primary response gene 88 (MyD88), Nucleotide Binding oligomerization domain containing protein 1 (NOD1), and combinations thereof.

15. The method of claim 12, wherein the animal is a companion animal.

16. The method of claim 15, wherein the companion animal is a feline.

17. The method of claim 15, wherein the companion animal is a canine.

18. The method of claim 12, wherein the first expression level and the second expression level are determined by measuring the levels of mRNA encoding the respective pattern recognition receptors.

19. The method of claim 12, wherein the oral health condition comprises at least one of gingivitis, periodontitis, dental plaque, dental tartar, pocket depth, mobile tooth, attachment loss, and gingival recession.

20. The method of claim 12, further comprising measuring a decrease of at least a two-fold change in the expression of the first expression level relative to the second expression level, wherein the decrease of at least a two-fold change in the expression level of the first expression level relative to the second expression level indicates the efficacy of the treatment, wherein the treatment of the oral health condition comprises subjecting the animal to a treatment designed to ameliorate the oral health condition.

* * * * *